US009821142B2

(12) United States Patent
Hannon et al.

(10) Patent No.: US 9,821,142 B2
(45) Date of Patent: Nov. 21, 2017

(54) URINARY CATHETERS WITH PROTECTIVE TIP

(71) Applicant: Hollister Incorporated, Libertyville, IL (US)

(72) Inventors: David Hannon, Ballina (IE); Colm Mulkerrin, Celbridge (IE); Michael G. Murray, Ballina (IE); Padraig M. O'Flynn, Castlegar (IE); Martin McMenamin, Lifford (IE); Adam J. Foley, Swords (IE)

(73) Assignee: Hollister, Incorporated, Libertyville, IL (US)

( * ) Notice: Subject to any disclaimer, the term of this patent is extended or adjusted under 35 U.S.C. 154(b) by 232 days.

(21) Appl. No.: 14/760,727

(22) PCT Filed: Mar. 13, 2014

(86) PCT No.: PCT/US2014/025364
§ 371 (c)(1),
(2) Date: Jul. 14, 2015

(87) PCT Pub. No.: WO2014/159869
PCT Pub. Date: Oct. 2, 2014

(65) Prior Publication Data
US 2015/0352321 A1 Dec. 10, 2015

Related U.S. Application Data

(63) Continuation-in-part of application No. 13/803,139, filed on Mar. 14, 2013, now Pat. No. 9,168,354.

(51) Int. Cl.
*A61M 25/00* (2006.01)
*A61M 25/01* (2006.01)

(52) U.S. Cl.
CPC ...... *A61M 25/0067* (2013.01); *A61M 25/001* (2013.01); *A61M 25/002* (2013.01);
(Continued)

(58) Field of Classification Search
CPC ............ A61M 25/001; A61M 25/0017; A61M 25/002; A61M 25/0067; A61M 25/0069;
(Continued)

(56) References Cited

U.S. PATENT DOCUMENTS 3,766,608 A 10/1973 Fay
3,991,444 A 11/1976 Bailey
(Continued)

FOREIGN PATENT DOCUMENTS

GB 2 356 816 A 9/1999
WO WO 2007/106431 A2 9/2007
(Continued)

OTHER PUBLICATIONS

Partial International Search for PCT Patent Appl'n. No. PCT/US2014/025364.
(Continued)

*Primary Examiner* — Adam Marcetich
(74) *Attorney, Agent, or Firm* — Cook Alex Ltd.

(57) ABSTRACT

A protective catheter tip has a generally tubular body portion defining an interior cavity. The proximal end of a urinary catheter is at least partially received within the protective tip, with the protective tip being retained on the urinary catheter without the need for a sleeve connecting the protective tip and the catheter. The protective tip may include a projection received within a draining hole or eye at the proximal end of the catheter to retain the protective tip on the catheter. The protective tip may instead include one or more projections that apply a frictional force to an outer surface of the catheter to retain the protective tip on the catheter. The protective tip (Continued)

may instead be retained on the catheter by a tether extending between the protective tip and a distal end of the catheter. The protective tip may also be provided in two pieces.

13 Claims, 16 Drawing Sheets

(52) U.S. Cl.
CPC .... *A61M 25/0017* (2013.01); *A61M 25/0069* (2013.01); *A61M 25/013* (2013.01); *A61M 25/0111* (2013.01); *A61M 25/0113* (2013.01); *A61M 25/0119* (2013.01)

(58) Field of Classification Search
CPC .......... A61M 25/0111; A61M 25/0113; A61M 25/013; A61M 2037/0038; A61M 25/0138; A61M 25/0119
See application file for complete search history.

(56) References Cited

U.S. PATENT DOCUMENTS

| | | | |
|---|---|---|---|
| 4,377,887 A | | 3/1983 | Valestin |
| 4,601,713 A | * | 7/1986 | Fuqua ............... A61M 25/0023 604/103.14 |
| 4,630,609 A | * | 12/1986 | Chin ................... A61M 25/104 604/101.01 |
| 4,862,560 A | | 9/1989 | Lichtenberg |
| 5,084,036 A | | 1/1992 | Rosenbaum |
| 5,147,341 A | | 9/1992 | Starke et al. |
| 5,653,700 A | | 8/1997 | Byrne et al. |
| 5,746,745 A | * | 5/1998 | Abele ..................... A61F 2/958 604/103.08 |
| 5,792,114 A | | 8/1998 | Fiore |
| 6,004,305 A | | 12/1999 | Hursman et al. |
| 6,053,905 A | | 4/2000 | Daignault, Jr. et al. |
| 6,070,304 A | | 6/2000 | Lii |
| 6,090,075 A | | 7/2000 | House |
| 6,148,488 A | * | 11/2000 | Gristock ............... E04H 15/646 160/392 |
| 6,217,569 B1 | * | 4/2001 | Fiore ................. A61M 25/0017 604/171 |
| 6,391,010 B1 | | 5/2002 | Wilcox |
| 6,402,726 B1 | | 6/2002 | Genese |
| 6,471,268 B1 | | 10/2002 | Stenstrom et al. |
| 6,578,709 B1 | | 6/2003 | Kavanagh et al. |
| 6,602,244 B2 | | 8/2003 | Kavanagh et al. |
| 7,311,698 B2 | | 12/2007 | Tanghoj et al. |
| 7,458,964 B2 | | 12/2008 | Mosler et al. |
| 7,601,158 B2 | | 10/2009 | House |
| 7,717,902 B2 | | 5/2010 | Sauer |
| 7,938,807 B2 | | 5/2011 | House |
| 7,938,838 B2 | | 5/2011 | House |
| 8,177,772 B2 | | 5/2012 | Christensen et al. |
| 8,177,774 B2 | | 5/2012 | House |
| 8,282,624 B2 | | 10/2012 | Tanghoej et al. |
| 2001/0007060 A1 | * | 7/2001 | Fiore ................. A61M 25/0017 604/171 |
| 2001/0044595 A1 | * | 11/2001 | Reydel ..................... A61F 2/95 604/98.02 |
| 2002/0103460 A1 | | 8/2002 | Kubalak |
| 2003/0199826 A1 | * | 10/2003 | Windheuser .......... A61M 25/00 604/161 |
| 2004/0220584 A1 | | 11/2004 | Muto et al. |
| 2005/0015076 A1 | | 1/2005 | Giebmeyer et al. |
| 2005/0197627 A1 | * | 9/2005 | Huang .................. A61M 25/00 604/171 |
| 2006/0122566 A1 | * | 6/2006 | Huang ............... A61M 25/0119 604/271 |
| 2006/0163097 A1 | * | 7/2006 | Murray ............. A61M 25/0009 206/364 |
| 2006/0278546 A1 | * | 12/2006 | State .................... A61M 25/002 206/364 |
| 2007/0088323 A1 | * | 4/2007 | Campbell ............. A61M 25/10 604/523 |
| 2009/0030370 A1 | * | 1/2009 | Nishtala ............ A61M 25/0017 604/103.01 |
| 2009/0070966 A1 | | 3/2009 | Gohlke et al. |
| 2009/0137986 A1 | | 5/2009 | Golden et al. |
| 2009/0224220 A1 | | 9/2009 | Jordan et al. |
| 2009/0249586 A1 | | 10/2009 | Brown |
| 2010/0137839 A1 | | 6/2010 | Copa |
| 2010/0256630 A1 | | 10/2010 | Faber |
| 2011/0172584 A1 | * | 7/2011 | Chin ..................... A61F 5/0076 604/8 |
| 2011/0213344 A1 | | 9/2011 | House |
| 2011/0213345 A1 | | 9/2011 | House |
| 2011/0213469 A1 | * | 9/2011 | Chin ..................... A61F 5/0076 623/23.65 |
| 2011/0230864 A1 | | 9/2011 | House |
| 2011/0313404 A1 | | 12/2011 | Amos et al. |
| 2012/0203211 A1 | | 8/2012 | Weadock et al. |
| 2013/0060234 A1 | * | 3/2013 | Besser ................. A61M 25/10 604/509 |
| 2014/0224678 A1 | * | 8/2014 | Schertiger ......... A61M 25/0017 206/210 |

FOREIGN PATENT DOCUMENTS

| | | |
|---|---|---|
| WO | WO 2010/006620 A1 | 1/2010 |
| WO | WO 2012/079581 A1 | 6/2012 |

OTHER PUBLICATIONS

Office Communication for U.S. Appl. No. 13/803,139, dated Oct. 21, 2014.
Office Communication for U.S. Appl. No. 13/803,139, dated Feb. 11, 2015.
Office Communication for U.S. Appl. No. 13/803,139, dated Apr. 30, 2015.

* cited by examiner

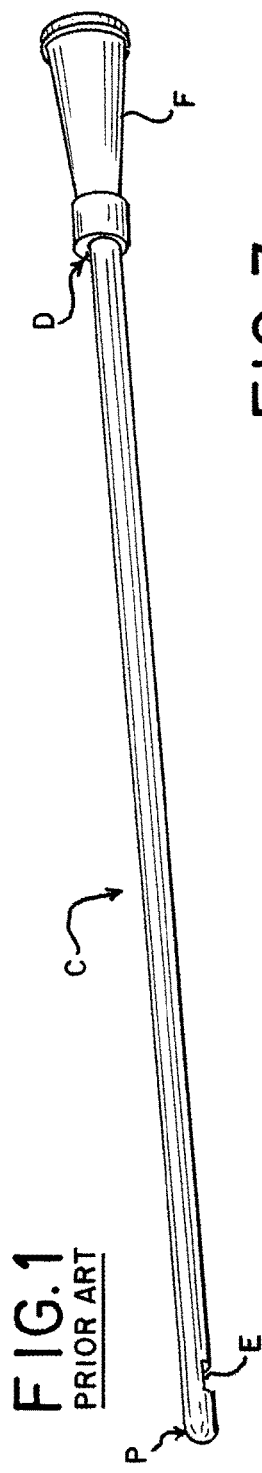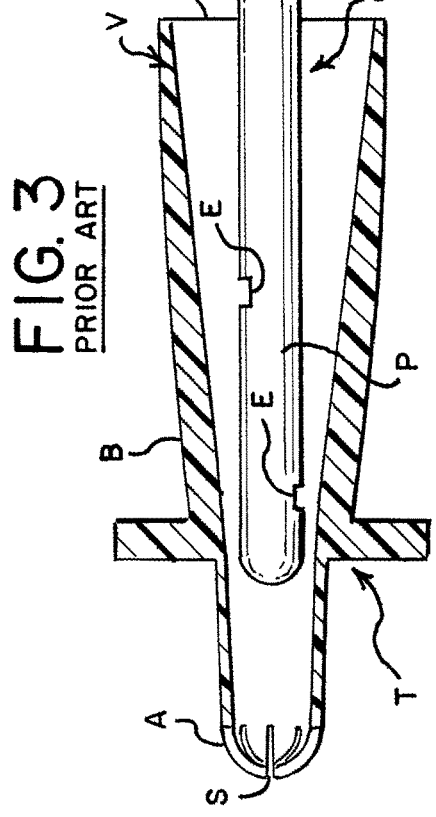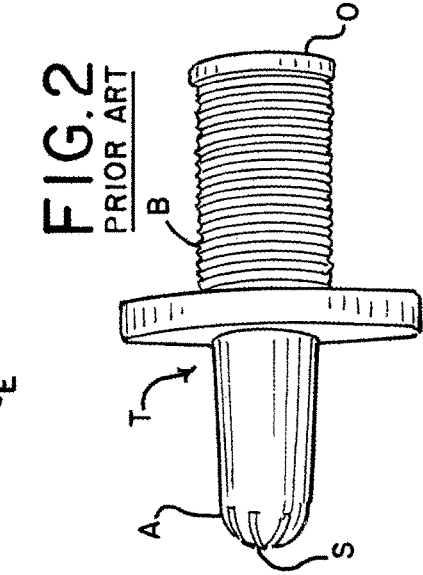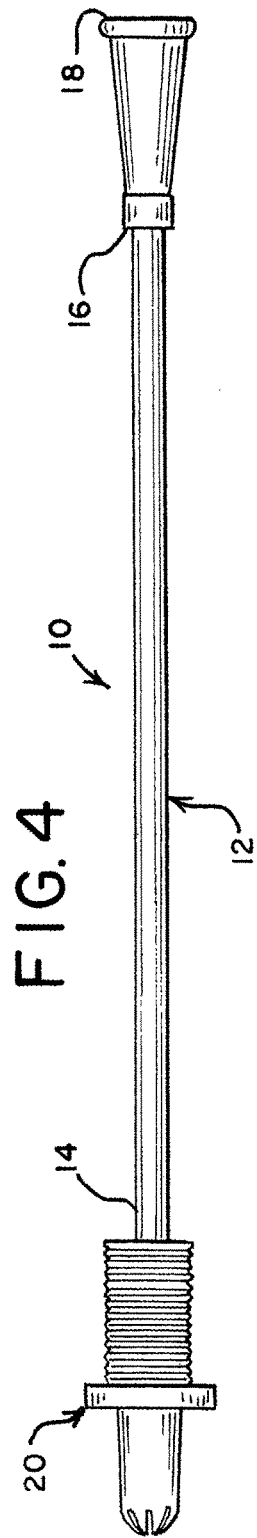

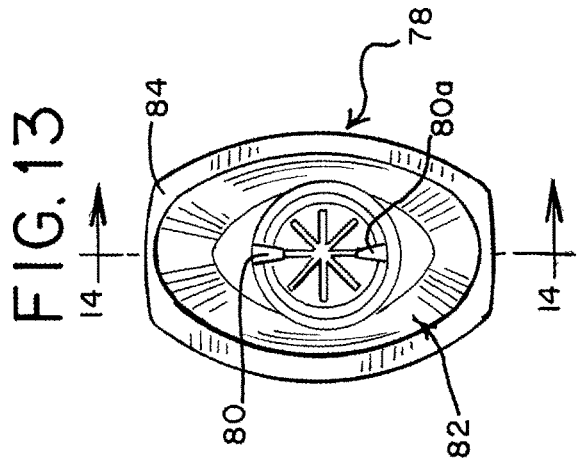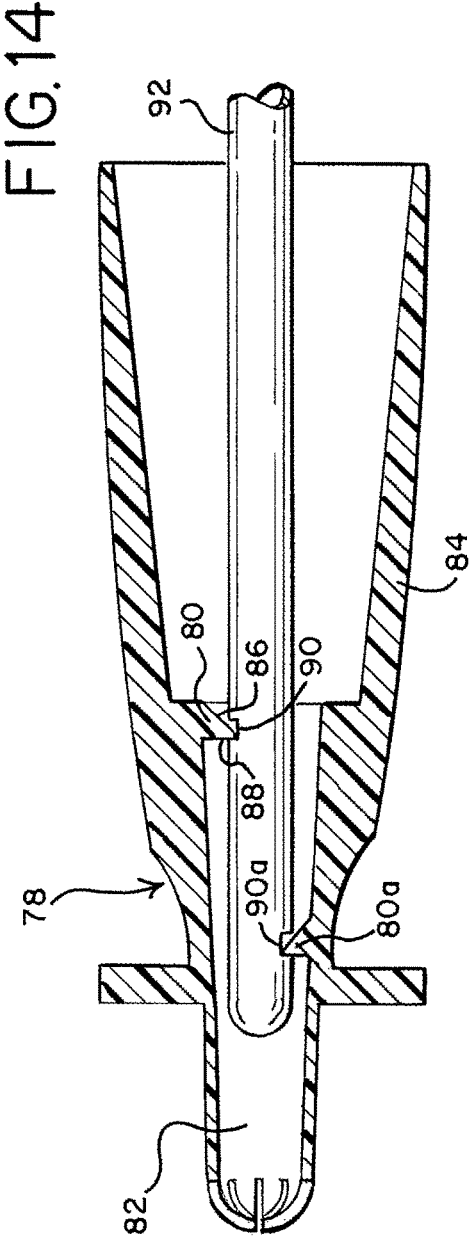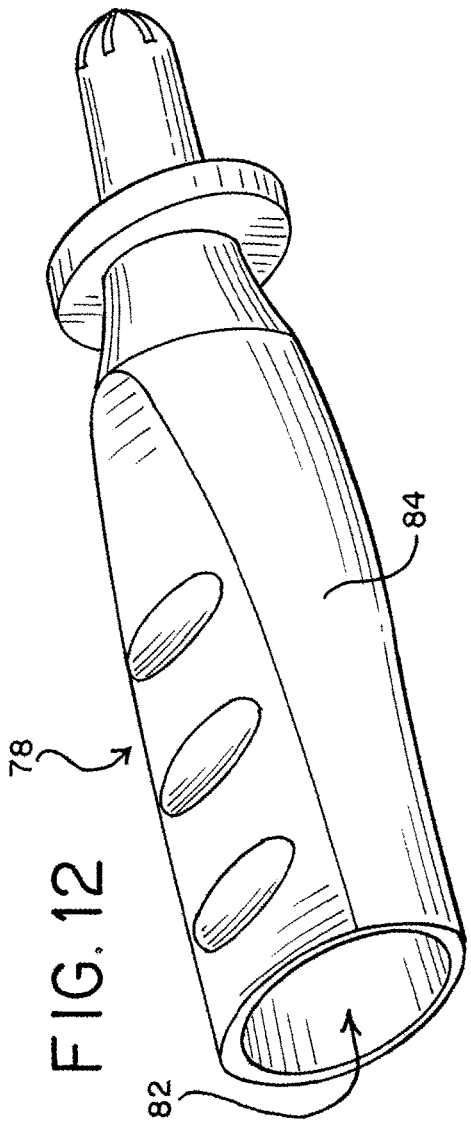

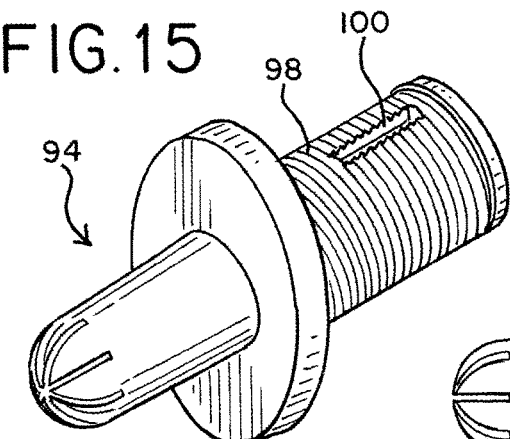
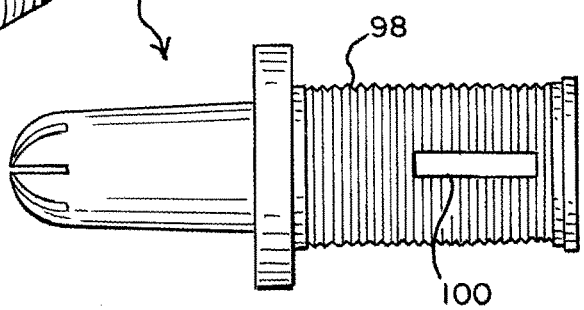
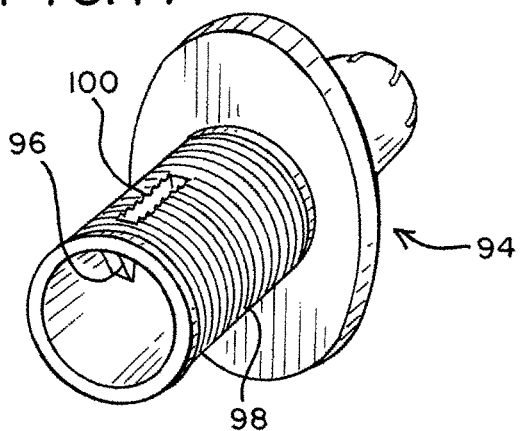
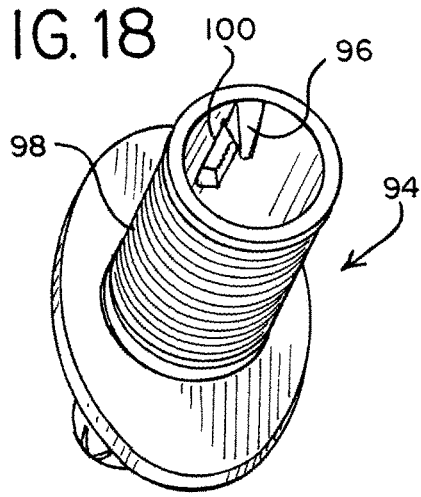
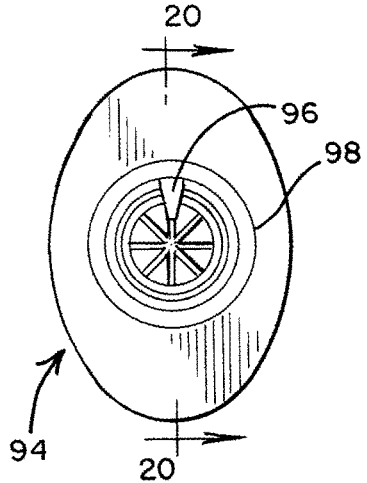
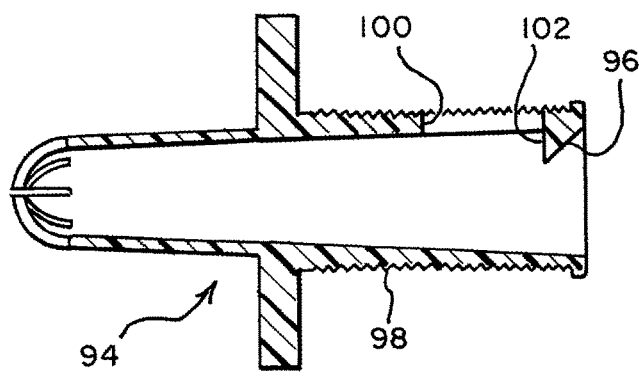

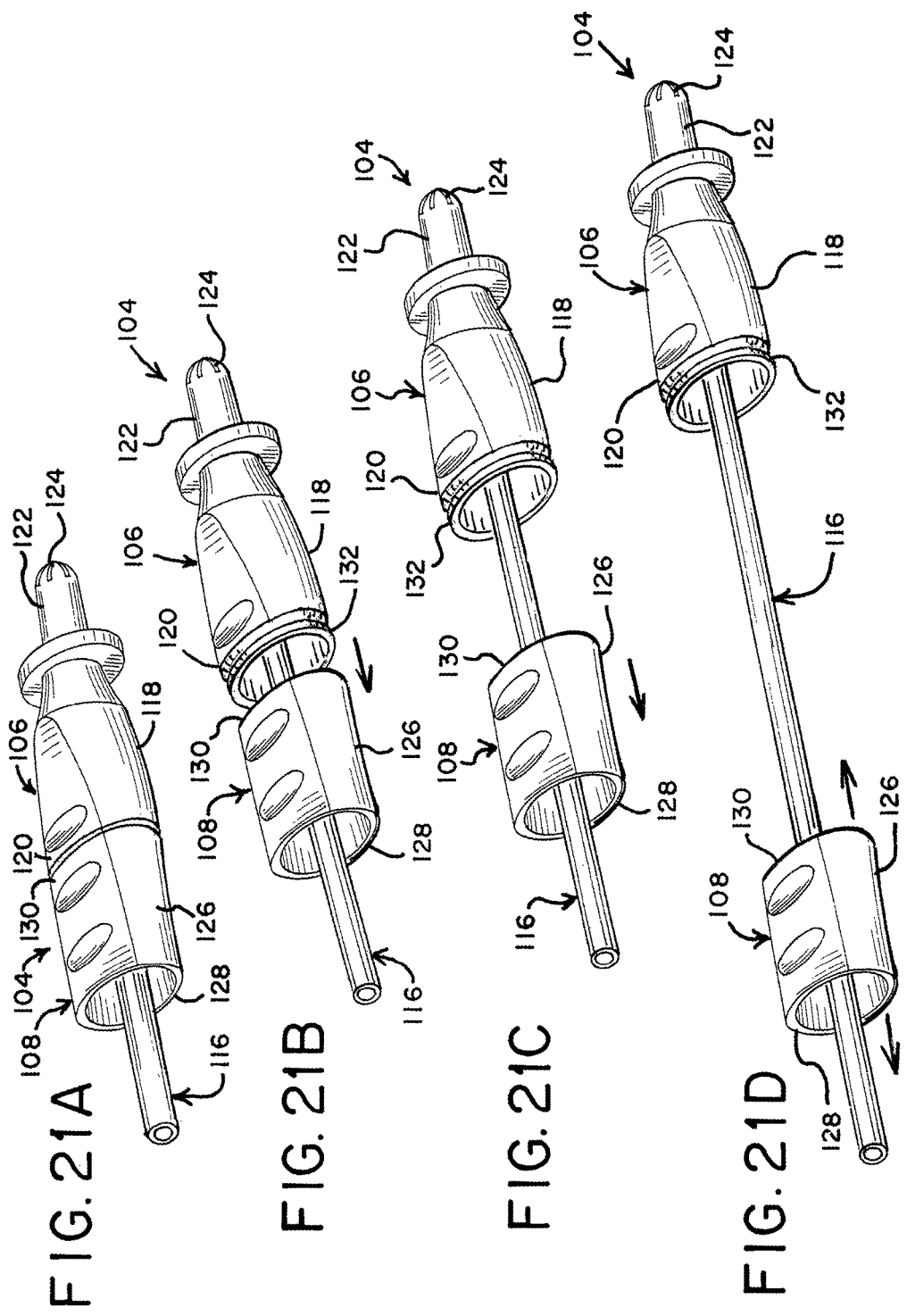

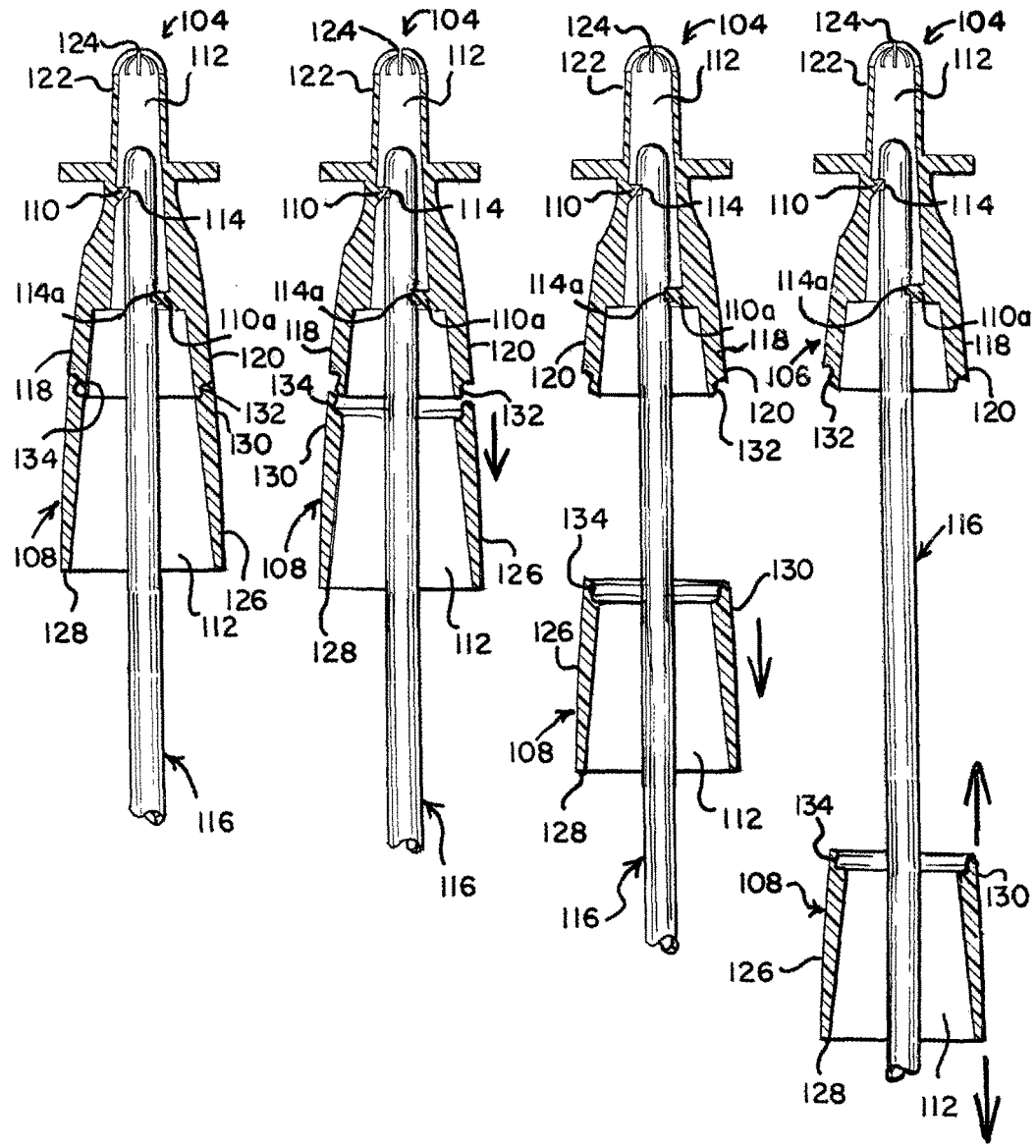

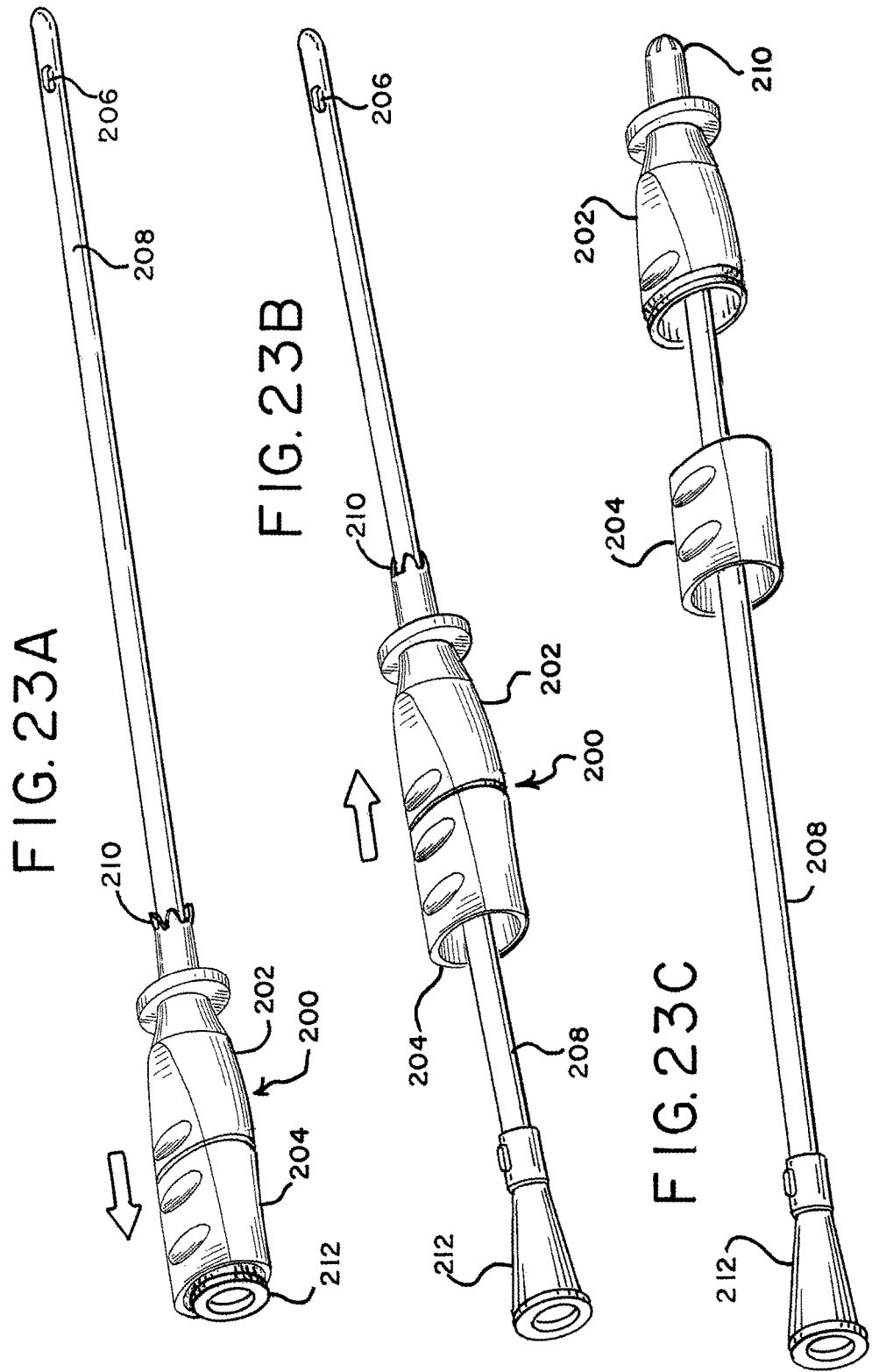

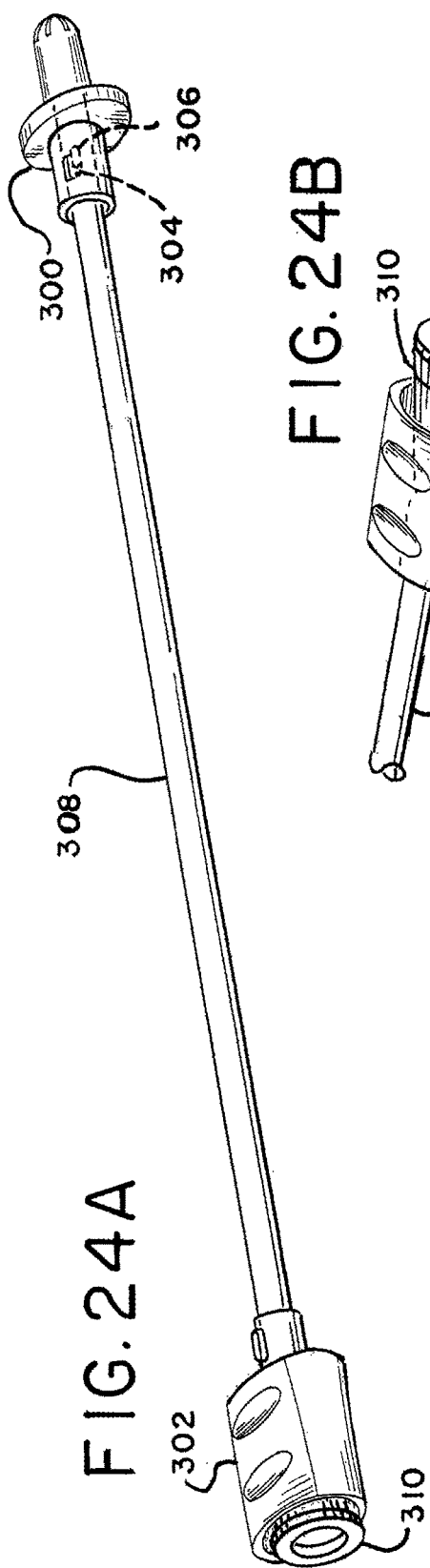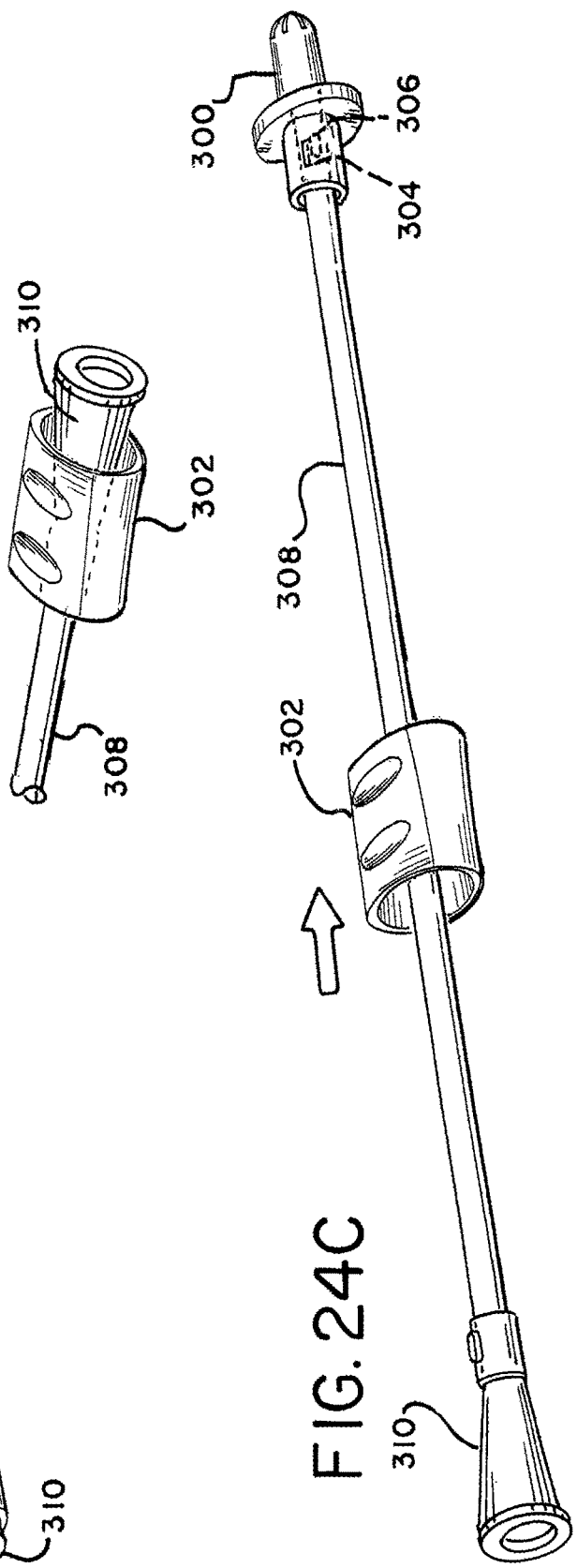

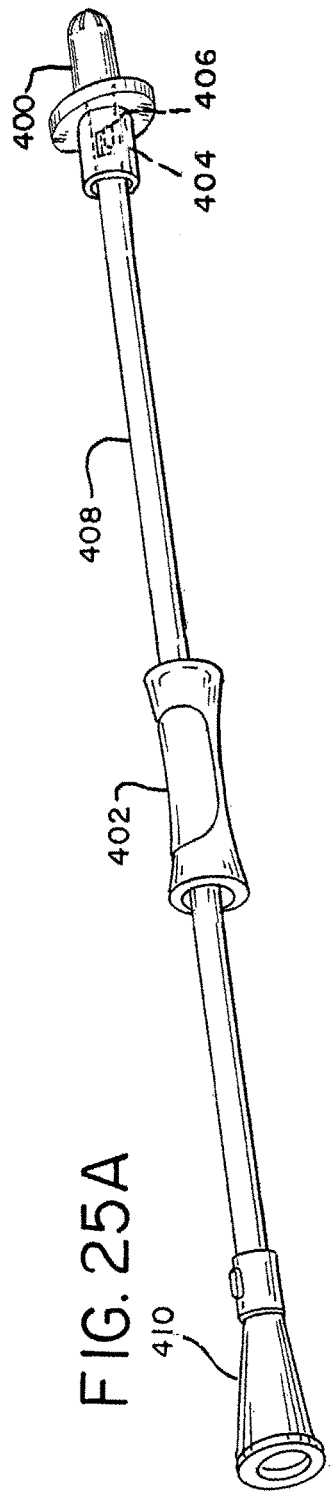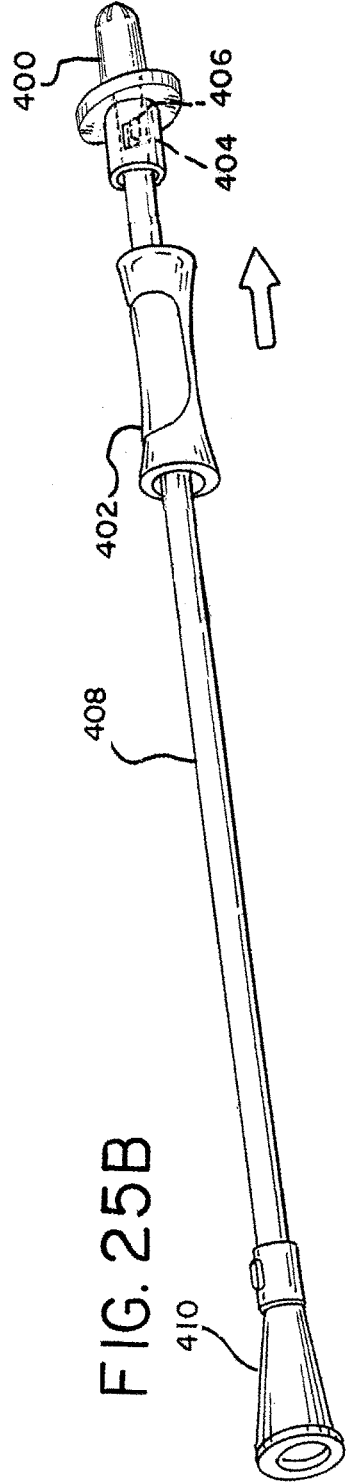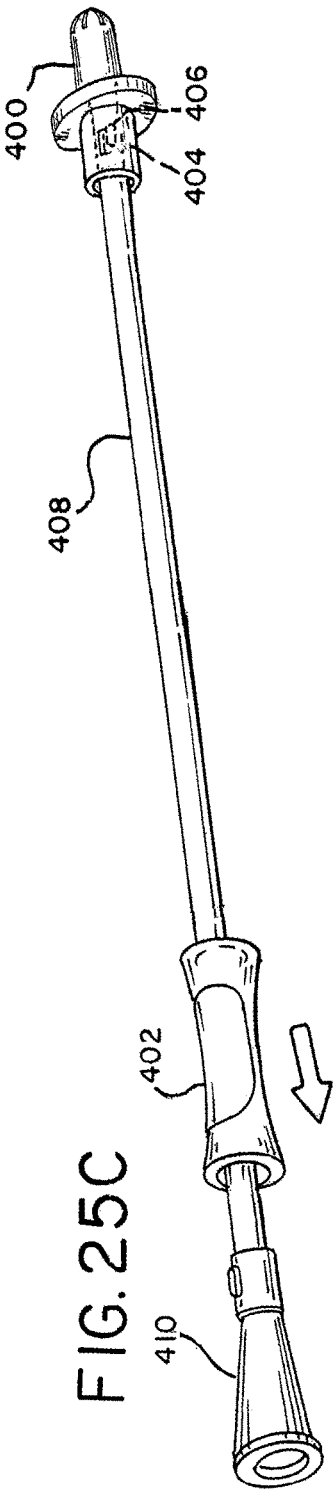

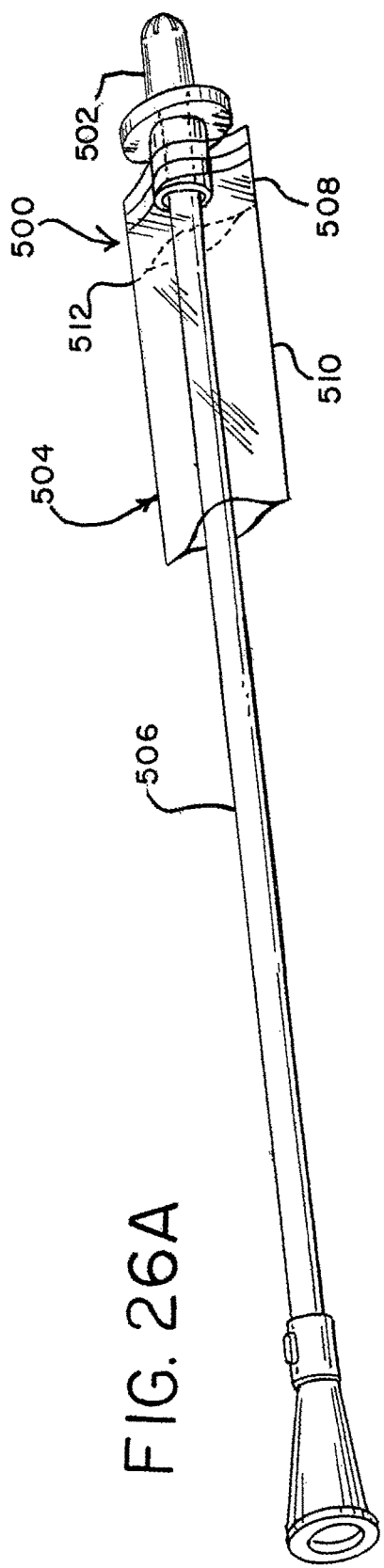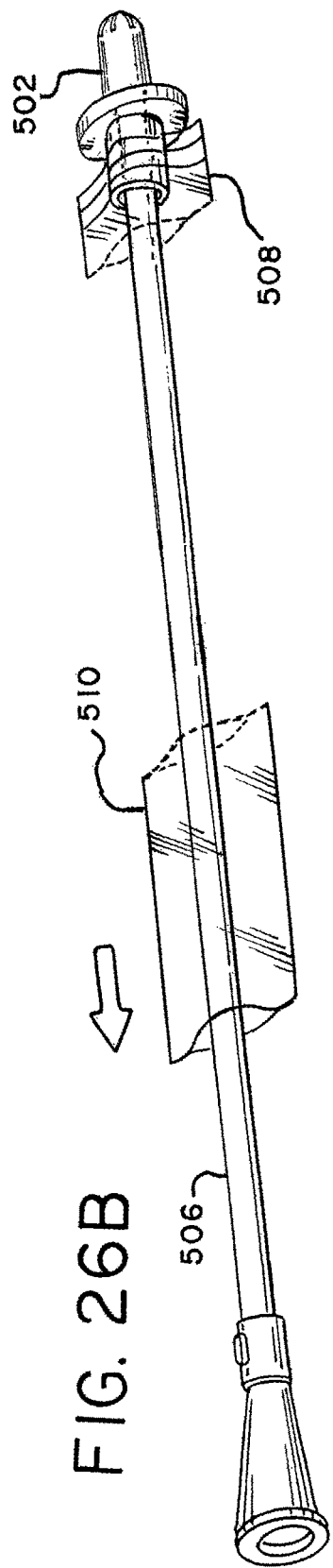

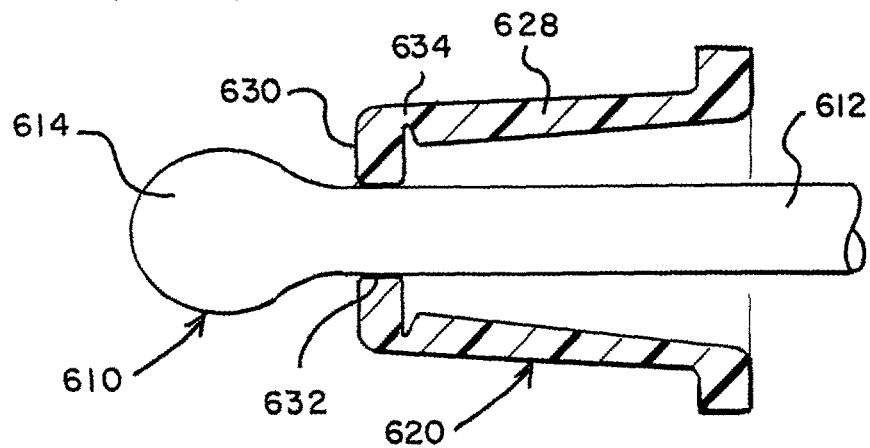
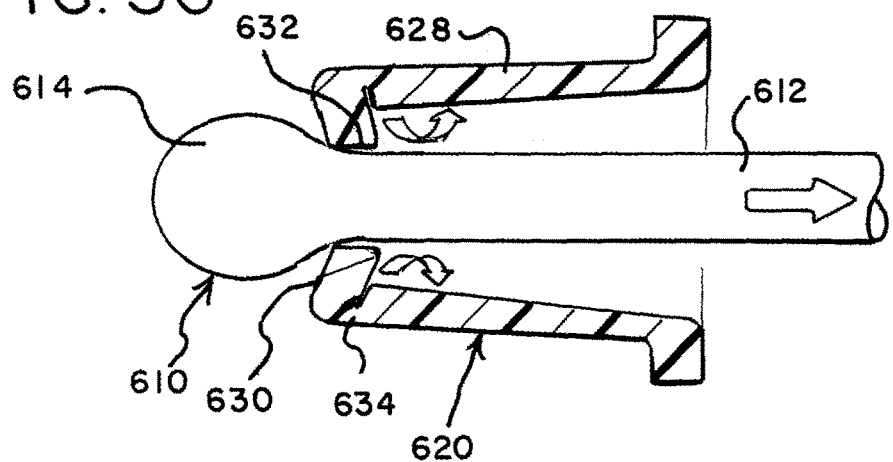
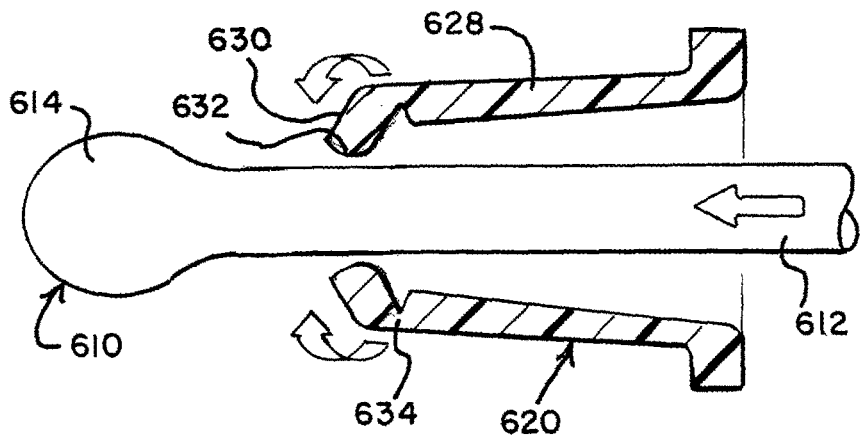

URINARY CATHETERS WITH PROTECTIVE TIP

RELATED APPLICATION

This application is a U.S. national stage application of PCT Patent Application Serial No. PCT/US2014/025364, filed Mar. 13, 2014, which claims the benefit of and priority of U.S. Non-Provisional patent application Ser. No. 13/803,139, filed Mar. 14, 2013, both of which are incorporated herein by reference.

DESCRIPTION

Technical Field

The present disclosure generally relates to urinary catheters. More particularly, the present disclosure relates to urinary catheter assemblies having a protective tip.

Background

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary incontinence. With the advent of intermittent catheters, individuals with urinary system abnormalities can self-insert and self-remove intermittent catheters several times a day. Such catheters typically include a shaft that is sufficiently flexible to navigate the curves of the urethra (especially catheters intended for male users), yet rigid enough to be pushed through the urethra without collapsing or "snaking" before an end of the catheter reaches the bladder.

An exemplary male urinary catheter C according to conventional design is shown in FIG. 1. A proximal end P of the catheter C includes draining holes or eyes E for the drainage of bodily fluids therethrough and into an internal conduit or lumen of the catheter C. The distal end D of the catheter may include a connecting member F, such as a funnel, for fluidly connecting the catheter C to a collection container, such as a collection bag into which urine drains.

The catheter C may be used in combination with a protective tip or cap or cover T (FIG. 2) that substantially encircles at least a portion of the proximal end P. FIG. 3 shows the proximal end P of the catheter C received within the protective tip T. The protective tip T has a generally tubular body portion B defining an interior cavity V (FIG. 3) that extends between an open end O and an access end A. The open end O is the end of the protective tip T into which the catheter C is inserted (in a direction toward the access end A). The access end A is movable between a generally closed condition when the proximal end P of the catheter C is positioned within the protective tip T (illustrated) and a generally open condition when the catheter C is advanced proximally (i.e., in a right-to-left direction in the orientation of FIG. 3) so as to pass through the access end A for advancement into and through the urethra. As shown in FIGS. 2 and 3, the access end A of the protective tip T may include one or more slits S, according to conventional design, that allow it to move between the generally closed and generally open conditions.

The protective tip T serves to isolate the proximal end P of the catheter C (including the eyes E) from the outside environment (e.g., from touch contamination whereby bacteria present on a user's hands might be transferred to the proximal end P of the catheter C) prior to insertion into the urethra and from the relatively high concentration of bacteria typically present in the distal urethra. By isolating the proximal end P of the catheter C from the outside environment, the sterility of the proximal end P may be maintained, thereby preventing bacteria from attaching to the proximal end P and being transferred to the urinary system. As shown in FIG. 3, the outer diameter of the catheter C may be smaller than the inner diameter of the protective tip T, such that there is a generally annular gap separating the catheter C and the protective tip T. Accordingly, to associate the protective tip T to the catheter C, a sleeve or cover (not illustrated) may be used to connect and secure together the protective tip T and the catheter C, thus preventing the protective tip T from detaching from the catheter C, and also to help protect the catheter C from touch contamination during handling and insertion.

FIGS. 2A and 3A illustrate another embodiment of a known protective tip T'. As in the embodiment of FIGS. 2 and 3, the protective tip or cap or cover T' substantially encircles at least a portion of the proximal end P of a catheter C, but does not have a closed access end A. Instead, the protective tip T' of FIGS. 2A and 3A has a generally tubular body portion B' defining an interior cavity V' (FIG. 3A) that extends between a distal open end O' and a proximal open end G. The distal open end O' is the end of the protective tip T' into which the catheter C is inserted (in a direction toward the proximal open end G). Unlike the access end A of FIGS. 2 and 3, the proximal open end G is not movable into a closed condition, but remains open during use. Accordingly, rather than serving to isolate the proximal end P of the catheter C from the outside environment, the protective tip T' serves as a gripper or gripping member that may be held by a user to manipulate and deploy the catheter C without directly handling the catheter C, and so may be referred to herein as a "gripper-type" protective tip. It should be noted that FIGS. 2 and 2A illustrate only two exemplary embodiments of known protective tips, and there are a number of other differently configured protective tips that are known and may be used in combination with the apparatus and methods described herein.

The present disclosure provides sleeveless urinary catheter assemblies with a protective tip, thereby avoiding the cost associating with manufacturing a sleeve and incorporating it into the catheter design.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a protective tip is provided for use in combination with a urinary catheter of the type having at least one eye. The protective tip includes a generally tubular body portion defining an interior cavity. At least one projection extends into the interior cavity of the body portion and is configured to be at least partially received by an eye of a urinary catheter at least partially positioned within the body portion.

In another aspect, a protective tip is provided for use in combination with a urinary catheter. The protective tip includes a generally tubular body portion defining an interior cavity and at least one projection extending into the interior cavity of the body portion. The projection may be configured to apply a generally uniform frictional force to an outer surface of a urinary catheter at least partially positioned within the body portion during use of the protective tip and the urinary catheter.

In yet another aspect, a urinary catheter assembly includes a protective tip, a urinary catheter, and a tether. The urinary catheter extends between proximal and distal ends, with the proximal end being at least partially receivable within the protective tip. The tether extends between the protective tip and the distal end of the urinary catheter.

In another aspect, a urinary catheter assembly includes a urinary catheter and a protective tip received on the urinary catheter. The protective tip includes a proximal piece and a distal piece, with the distal piece being separate from or detachably connected to the proximal piece.

In yet another aspect, a protective tip is provided for use in combination with a urinary catheter having a proximal extension with an enlarged end and a necked-down section positioned adjacent to and distally of the enlarged end. The protective tip includes an outer member and an insert at least partially received within the outer member. The insert includes a generally radially inwardly extending projection configured to be positioned distally of the enlarged end of the urinary catheter and to contact the enlarged end of the urinary catheter to resist distal movement of the urinary catheter with respect to the protective tip.

In another aspect, a urinary catheter assembly includes a urinary catheter having a proximal end portion with at least one eye. A protective sleeve tip defines an interior cavity receiving the proximal end portion of the urinary catheter. The protective sleeve tip is formed of a thin film material and includes at least one projection extending into the interior cavity and at least partially received by the at least one eye of the urinary catheter.

BRIEF DESCRIPTION OF THE DRAWINGS

FIG. 1 is a perspective view of a male urinary catheter according to a known design;

FIG. 2 is a side elevational view of a protective catheter tip according to a known design;

FIG. 3 is a cross-sectional view of a distal end of the catheter of FIG. 1, received within the protective tip of FIG. 2;

FIG. 4 is a side elevational view of an embodiment of a sleeveless urinary catheter assembly having a protective tip, according to an aspect of the present disclosure;

FIG. 12 is a perspective view of a protective catheter tip configured for use in a sleeveless urinary catheter assembly, according to an aspect of the present disclosure;

FIG. 13 is an end view of the protective tip of FIG. 12;

FIG. 14 is a cross-sectional view of the protective tip of FIG. 12, taken through the line 14-14 of FIG. 13 and showing a catheter positioned within the protective tip;

FIG. 15 is a perspective view of an alternative embodiment of the protective tip of FIG. 12;

FIG. 16 is a top plan view of the protective tip of FIG. 15;

FIGS. 17 and 18 are rear perspective views of the protective tip of FIG. 15;

FIG. 19 is an end view of the protective tip of FIG. 15;

FIG. 20 is a cross-sectional view of the protective tip of FIG. 15, taken through the line 20-20 of FIG. 19;

FIGS. 21A-21D are perspective views of a two-piece protective tip and illustrate a method of separating the two pieces of the protective tip;

FIGS. 22A-22D are cross-sectional views of and further illustrate the two-piece protective tip and method of FIGS. 21A-21D;

FIGS. 23A-23C are perspective views of another embodiment of a two-piece protective tip, with the protective tip being configured for positioning at a distal end of the associated catheter prior to use;

FIGS. 24A-24C are perspective views of yet another embodiment of a two-piece protective tip, with a distal piece of the protective tip being configured for positioning at a distal end of the associated catheter and a proximal piece positioned at a proximal end of the catheter prior to use;

FIGS. 25A-25C are perspective views of another embodiment of a two-piece protective tip, with a distal piece of the protective tip being configured for positioning at a midsection or intermediate portion of the associated catheter and a proximal piece positioned at a proximal end of the catheter prior to use;

FIGS. 26A and 26B are perspective views of yet another embodiment of a two-piece protective tip, with a distal piece of the protective tip being a frangible partial sleeve;

FIG. 29 is a cross-sectional, detail view of an insert of the protective tip and a proximal end of the urinary catheter of FIG. 27;

FIG. 30 is a cross-sectional, detail view of the insert and urinary catheter proximal end of FIG. 29, with the urinary catheter proximal end moving in a distal direction with respect to the insert;

FIG. 31 is a cross-sectional, detail view of the insert and urinary catheter proximal end of FIG. 29, with the urinary catheter proximal end moving in a proximal direction with respect to the insert;

DETAILED DESCRIPTION OF THE ILLUSTRATED EMBODIMENTS

Figure 2A:
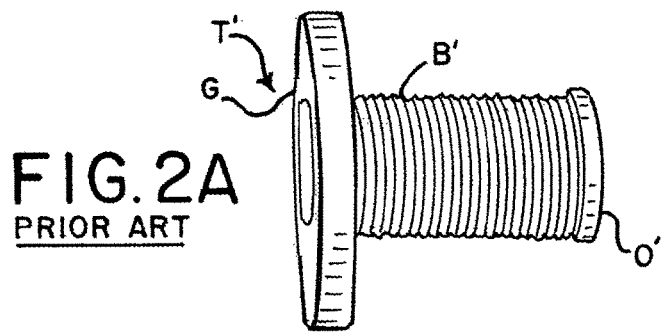
FIG. 2A is a side elevational view of another embodiment of a protective catheter tip according to a known design.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

FIG. 4 shows a sleeveless urinary catheter assembly 10 according to the present disclosure. The sleeveless urinary catheter assembly 10 includes a urinary catheter 12, which extends between a proximal end 14 and a distal end 16. In the illustrated embodiment, the urinary catheter 12 is provided according to conventional design (e.g., according to the design illustrated in FIG. 1 and discussed above), which may be advantageous for retrofitting on-hand catheters into sleeveless assemblies. However, it is also within the scope for the urinary catheter 12 to have a novel design. Additionally, while it may be advantageous or preferred for the urinary catheter assemblies described herein to omit a protective sleeve, it is also within the scope of the present disclosure for the features and aspects described herein to be employed in combination with urinary catheter assemblies which include a protective sleeve.

The illustrated urinary catheter 12 is an elongated, hollow shaft or tube having a closed proximal insertion end portion 14 (as in FIG. 1) and an open distal end portion 16. The proximal end 14 includes a hemispherical or otherwise atraumatic tip that is suitable for insertion into and passage through a body lumen or passageway of the body, such as the urethra, for example. As described above, the proximal end 14 of the catheter 12 includes draining holes or eyes (as in FIG. 1), while the distal end 16 includes a connecting member, such as a funnel. Unless stated to the contrary, the urinary catheters and sleeveless urinary catheter assemblies described herein may be adapted for either male or female use.

The sleeveless urinary catheter assembly 10 of FIG. 4 further includes a protective tip or cap or cover 20 that substantially encircles at least a portion of the proximal end 14 of the catheter 12. As will be described in greater detail, the protective tip 20 may be provided having an external appearance generally according to conventional design (e.g., according to the design illustrated in FIGS. 2 and 2A) or may have a novel design. For example, it may be preferred to employ a modified design that is longer than typical protective tips for improved gripping, such as the protective tip 20 of FIGS. 12 and 12A. In either case, the protective tip 20 may be retained upon the proximal end 14 of the catheter 12 without the presence of a sleeve or cover, which may be accomplished in any of a variety of ways.

Figure 5:
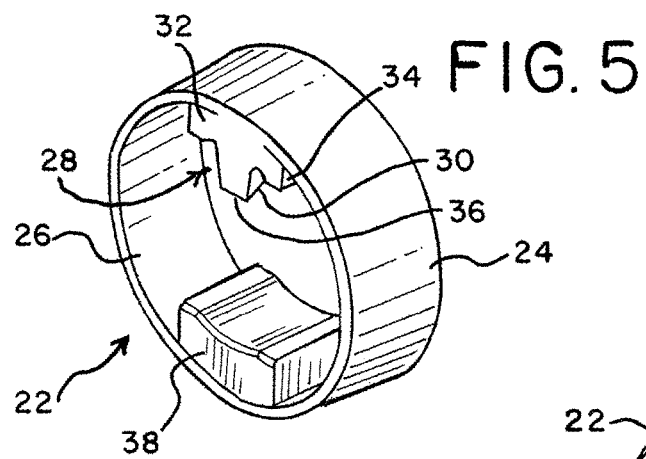
FIG. 5 is a perspective view of an insert or adapter for associating a protective tip to a urinary catheter.
Figure 6:
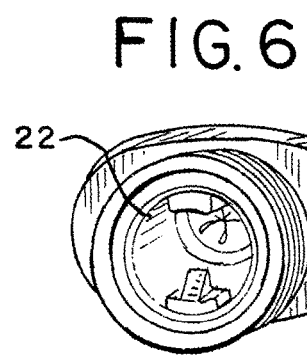
FIG. 6 is an end view of the insert or adapter of FIG. 5 at least partially received within a protective tip of the type illustrated in FIG. 2.
Figure 7:
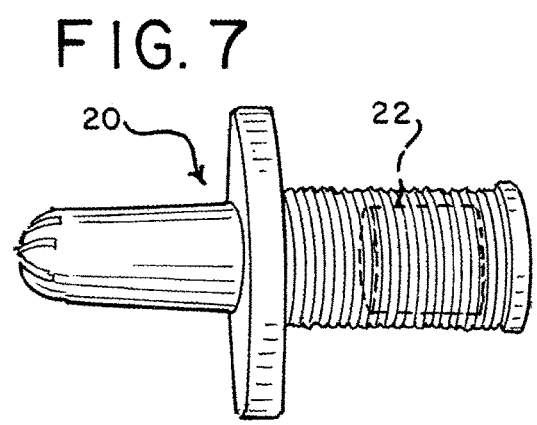
FIG. 7 is a side elevational view of a protective tip of the type illustrated in FIG. 2, with the insert or adapter of FIG. 5 at least partially received therein and shown in broken lines.

According to one method of securing the protective tip 20 to the catheter 12, the sleeveless urinary catheter assembly includes an insert or adaptor that engages both a portion of the protective tip 20 and a portion of the catheter 12. FIG. 5 shows an exemplary embodiment of such an insert 22, while FIGS. 6 and 7 show the insert 22 fully received within an interior cavity of the protective tip 20. In the illustrated embodiment, the insert 22 is generally annular, with an outer surface 24 that engages or bears against an inner surface of the protective tip 20. The insert 22 may be provided so as to be held in place by a friction fit or interference fit when positioned within the protective tip 20 and/or it may be held in place by an adhesive or the like.

The inner surface 26 of the insert 22 includes an inwardly directed projection 28. The projection 28 is configured to be at least partially received by an eye of a catheter 12 when the proximal end 14 of the catheter 12 is positioned within the protective tip 20. FIG. 14 shows a modified protective tip (which will be discussed in greater detail herein) having projections extending into both eyes of the catheter, and it should be understood that the projection 28 of the insert 22 is received by one of the catheter eyes in the same manner. By extending at least one projection into an eye of the catheter 12, the proximal end 14 of the catheter 12 is held in place inside the protective tip 20 without the need for a sleeve or cover to connect the protective tip 20 to the catheter 12. Although the insert 22 is shown with a single projection 28, it is within the scope of the present disclosure to provide more than one projection. For example, the insert may include a second projection configured to be at least partially received by a second eye of the catheter 12.

The illustrated projection 28 extends in a generally radial inward direction, with an inclined surface 30 and a radial surface 32. While the inclined surface 30 and the radial surface 32 are illustrated as generally planar surfaces, they may be convex or curved or otherwise contoured. When the insert 22 is received within the protective tip 20, the inclined surface 30 faces toward the open end of the protective tip 20, while the radial surface 32 faces the access end of the protective tip 20 (as in FIGS. 14 and 14A). To deploy the catheter 12 into a urethra, it is advanced proximally, in the direction of the access end. The inclined surface 30, if provided, allows the catheter 12 to more easily move in this direction, by deforming the catheter 12 and/or the projection 28 as the catheter 12 presses against the inclined surface 30, thereby allowing the projection 28 to disengage from the eye upon sufficient proximal movement of the catheter 12. In addition to disengaging the projection 28 from the eye upon relative proximal movement of the catheter 12, it is also possible for the projection 28 to be configured such that twisting or rotation of the catheter 12 about its central axis is also sufficient to disengage the projection 28 from the catheter eye.

In one embodiment, the projection 28 (or at least the portion of it that is received by the catheter eye) may be relatively thin compared to the width of the eye to provide less resistance to proximal advancement of the catheter. For example, in the embodiment illustrated in FIG. 5, the projection 28 includes a relatively wide base portion 34 and a relatively thin end portion 36. In such an embodiment, the base portion does not extend into the catheter eye, but instead provides additional strength to the projection 28 and may also help to orient the catheter 12 with respect to the projection 28, as will be described in greater detail herein. The thinner end portion 36 may be adapted to provide the desired amount of resistance to proximal or rotational movement of the catheter 12 with respect to the projection 28.

As for the radial surface 32 of the projection 28, it serves to prevent or at least hinder distal movement of the catheter 12 with respect to the projection 28 (i.e., movement toward the open end of the protective tip 20). More particularly, the radial surface 32 contacts the perimeter of the eye to effectively catch the eye and prevent the projection 28 from being removed from the eye by distal movement of the catheter 12. In other embodiments, the projection may be differently configured, for example, by having two inclined surfaces or two radial surfaces or two or more non-inclined, non-radial surfaces.

In addition to the dimensions of the projection 28 and the extent to which it extends into the catheter eye, the material composition of the projection 28 may also affect the resistance to movement that it provides. A relatively rigid material (or combination of materials) may be used if additional resistance is desired, whereas a relatively flexible material (or combination of materials) may be used if less resistance is required. In one embodiment, it was found that a projection 28 formed of silicone provided an advantageous combination of rigidity and flexibility, but other materials may also be used without departing from the scope of the present disclosure.

Figure 3A:
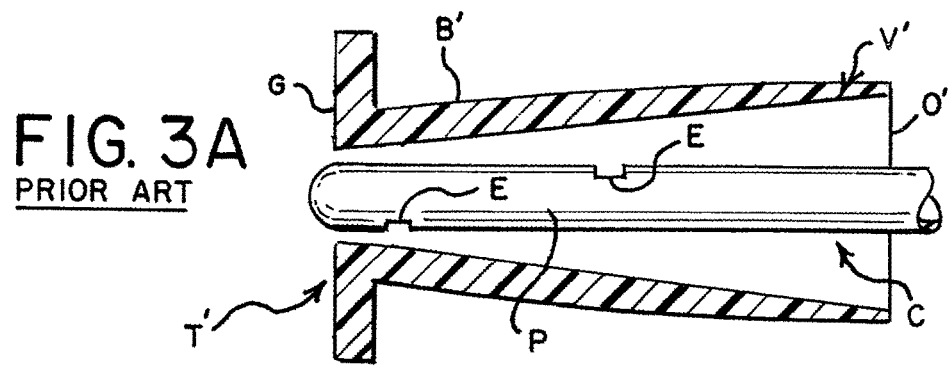
FIG. 3A is a cross-sectional view of a distal end of the catheter of FIG. 1, received within the protective tip of FIG. 2A.

The inner surface 26 of the insert 22 may further include an inwardly extending guide or spacer 38. As shown in FIG. 3, there is typically a gap between the inner surface of the protective tip and the outer surface of the catheter when the catheter is received within the protective tip. If provided, a guide or spacer 38 inhabits the gap between the protective tip 20 and the catheter 12, thereby helping to maintain the catheter 12 in a relatively coaxial relationship with the protective tip 20. The extent to which the projection 28 extends into the catheter eye has an effect upon the resistance that the catheter 12 experiences when moving proximally or distally, so by controlling the position of the catheter 12 with respect to the protective tip 20 (i.e., by maintaining them in a generally coaxial relationship), the interaction between the projection 28 and the eye can be better controlled. As described above, the projection 28 itself may also include a portion (e.g., a base portion 34) that serves a similar purpose to the guide 38, by occupying at least part of the space between the inner surface of the protective tip 20 and the outer surface of the catheter 12 to help orient the catheter 12 coaxially with respect to the protective tip 20.

Figure 8:
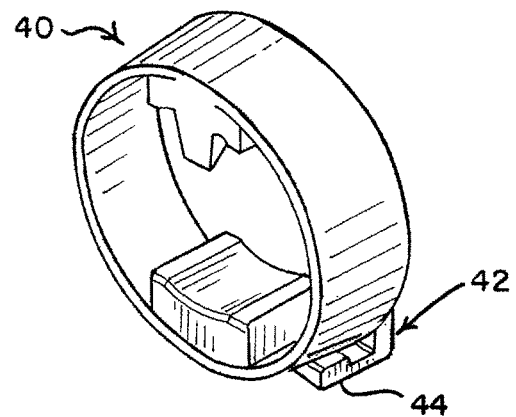
FIG. 8 is a perspective view of an alternative embodiment of the insert or adapter of FIG. 5.

According to an alternative embodiment of the insert 22 of FIGS. 5-7, the insert may be provided with alternative means for securing it with respect to the protective tip 20. For example, in the embodiment of FIG. 8, an insert 40 is provided substantially according to the foregoing description of the insert 22 of FIGS. 5-7 with the exception that the insert 40 includes a hook or clip 42 that may engage the open end of the protective tip 20. In one embodiment, the clip 42 is generally C- or L-shaped (when viewed from the side), extending from the outer surface or one of the ends (e.g., the distal end) of the insert 40. The insert 40 may be secured to the protective tip 20 by pressing it proximally into the interior cavity of the protective tip 20 via the open end. A radially outward portion or leg 44 of the clip 42 remains outside of the interior cavity and engages the outer surface of the protective tip 20 to pinch or squeeze the protective tip 20 against the insert 40, thereby retaining the insert 40 in place. Other clip configurations or other means for securing an insert to a protective tip may also be employed without departing from the scope of the present disclosure.

Figure 9:
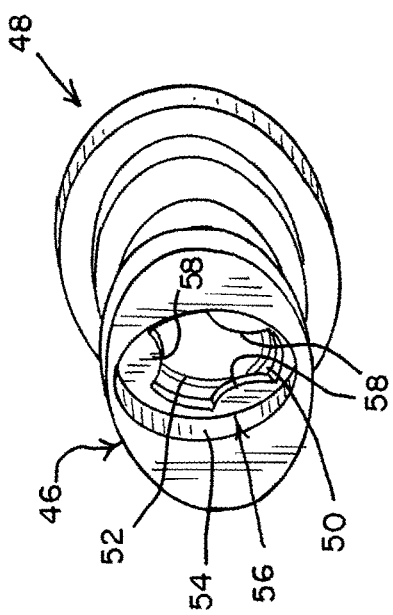
FIG. 9 is a perspective view of another embodiment of a protective catheter tip according to a known design.

According to another aspect of the present disclosure, a protective tip may be secured to a catheter by a friction or interference fit, rather than by a projection extending into an eye of the catheter. For example, FIG. 9 shows the open distal end 46 of a protective tip 48. The protective tip 48 may be provided according to conventional design (e.g., according to the design illustrated in FIGS. 2 and 2A) or any other suitable design. At the distal end 46 of the protective tip 48, the interior cavity of the protective tip 48 includes a generally radial wall 50 that defines a central opening or aperture 52 configured to receive the proximal end of a catheter. The diameter of the central opening 52 is selected to be sufficiently large so as to allow a catheter received therein to slide proximally and distally with respect to the protective tip 48.

Figure 10:
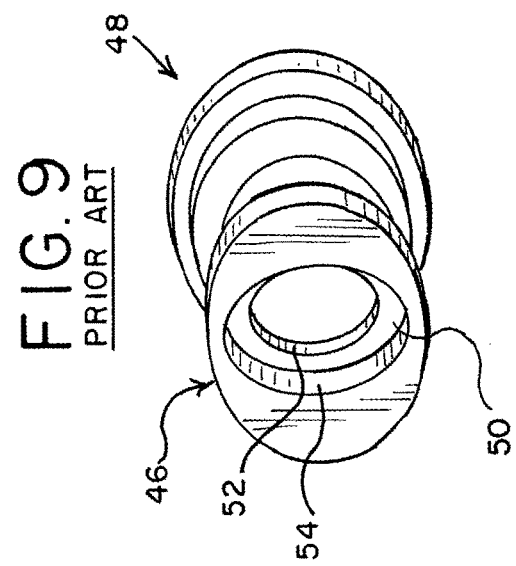
FIG. 10 is a perspective view of a protective tip of the type illustrated in FIG. 9, with an insert or adapter according to an aspect of the present disclosure associated therewith.

In the illustrated embodiment, the central opening 52 is surrounded by an upstanding collar or rim 54 having a larger inner diameter than the central opening 52 and defining a distal portion of the interior cavity of the protective tip 48. According to an aspect of the present disclosure, an insert or adaptor 56 is received within the collar 54, as shown in FIG. 10. The insert 56 includes at least one projection 58 that extends in a generally inward radial direction to bear against the outer surface of a catheter received within the protective tip 48. In the illustrated embodiment, the insert 56 includes three projections 58 that are spaced equally along the inner perimeter of the generally annular insert 56. In other embodiments, the insert may include fewer or more than three projections 58, which may be spaced symmetrically or asymmetrically about the inner perimeter of the insert 56. Additionally, while FIG. 10 shows three substantially identical arcuate or semicircular projections 58, it is also within the scope of the present disclosure for the projections to be differently configured.

The projections 58 provide a surface that bears against the outer surface of a catheter. The projections 58 combine to define a diameter or bearing surface that is smaller than the diameter of the central opening 52 of the distal end 46 of the protective tip 48. The diameter or bearing surface defined by the projections 58 is preferably sufficiently small to provide a generally uniform frictional force to the outer surface of the catheter, while still allowing the catheter to be moved proximally and distally with respect to the protective tip 48. Upon application of sufficient force (which may be determined by a number of factors including, but not limited to, the size of the bearing surface defined by the projections 58, the number of projections 58, and the material composition of the catheter and the insert 56), the catheter may be moved proximally and distally with respect to the protective tip 48. At applied forces that are less than the threshold amount (e.g., during transportation of the sleeveless urinary catheter assembly, routine handling prior to use, and handling to align the catheter with the urethra at the beginning of use), the bearing surface defined by the projections 58 provides a sufficiently great frictional force against the outer surface of the catheter so as to retain the protective tip 48 in place. When a sufficient force has been applied to the catheter and/or to the protective tip 48, the catheter moves proximally or distally with respect to the protective tip 48, but the projections 58 remain stationary and apply the same frictional force to the catheter.

The insert 56 may be secured to the protective tip 48 by means allowing it to be fully received within the interior cavity of the protective tip 48, such as a friction fit or interference fit or adhesive or the like. The insert 56 may alternatively be secured to the protective tip 48 by means extending at least partially outside of the interior cavity, such as a clip of the type shown in FIG. 8. Additionally, the insert 56 may be associated with a different portion of the protective tip 48 and it is not limited to receipt within a collar 54 at the distal end 46 of the protective tip 48.

Figure 11:
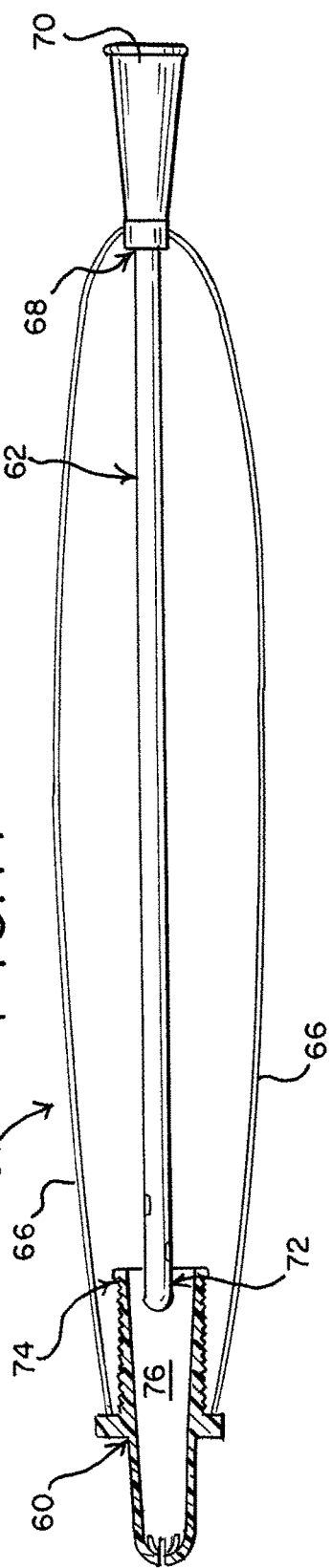
FIG. 11 is a cross-sectional view of a sleeveless urinary catheter assembly having a protective tip tethered to a distal end of a urinary catheter, according to an aspect of the present disclosure.

In accordance with another aspect of the present disclosure, rather than employing an insert or adaptor, the protective tip 60 and catheter 62 of a sleeveless urinary catheter assembly 64 are connected and secured together by a flexible element or filament or tether 66 (FIG. 11). In the embodiment of FIG. 11, an elongated tether 66 defines a loop attached to a portion of the protective tip 60 and the distal end 68 (particularly, the funnel 70) of the catheter 62. The tether 66 may have both ends connected to the protective tip 60 or to the catheter 62, with a midsection of the tether 66 being secured to the other component of the sleeveless urinary catheter assembly 64 by suitable means (e.g., adhesive or by receiving the tether 66 in a groove or channel or other retaining formation). Alternatively, the tether 66 may define a closed loop, having its ends connected to each other to form a complete circle, in which case both the protective tip 60 and the catheter 62 may include a groove or channel or other retaining formation to receive the tether 66 or an adhesive to secure the tether 66.

In another embodiment, rather than using a single tether, a plurality of tethers may be used to connect and secure together the protective tip 60 and the catheter 62. If a plurality of tethers are provided, each tether may define a loop (either a closed loop or one having both ends attached to the protective tip 60 or the catheter 62) or instead have one end secured to each of the protective tip 60 and the catheter 62. If more than one tether is used, it may be advantageous for the tethers to be substantially identical to each other or to at least have substantially the same length for a symmetrical interconnection between the protective tip 60 and the catheter 62. However, it is within the scope of the present disclosure for a plurality of tethers to be differently configured.

Regardless of how many tethers are provided or how exactly they are configured, it is advantageous for them to be configured to prevent removal of the proximal end 72 of the catheter 62 from the open distal end 74 of the protective tip 60 without bending or otherwise deforming the catheter 62. In other words, the length of the tether(s) should be selected such that proximal end 74 of the catheter 62 remains at least partially within the interior cavity 76 of the protective tip 60 even upon distal movement of the catheter 62 with respect to the protective tip 60 (i.e., movement in a left-to-right direction in the orientation of FIG. 11) to the point at which the tether 66 becomes taut and prevents further movement in that direction. To decrease the risk of the catheter 62 being backed out of the protective tip 60, it may be preferred to employ a relatively rigid catheter, rather than one that is easily bendable or otherwise deformable. It may also be preferred to use such a catheter with the other sleeveless urinary catheter assemblies described herein, although other catheters may also be used without departing from the scope of the present disclosure.

According to yet another aspect of the present disclosure, the protective tip itself is adapted to be secured to the catheter in a sleeveless urinary catheter assembly. For example, FIGS. 12-14 show one embodiment of a protective tip 78 that is configured to maintain itself on the proximal end of a urinary catheter. In particular, the protective tip 78 includes at least one projection 80 extending into the interior cavity 82 defined by the generally tubular body portion 84 of the protective tip 78. The projection 80 may be configured according to the description of the projection 28 of FIG. 5, with an inclined surface 86 and a radial surface 88 configured to be at least partially positioned within an eye 90 of a urinary catheter 92 at least partially positioned within the body portion 84 (FIG. 14). In the embodiment of FIGS. 12-14, there are two projections (a distal projection 80 and a proximal projection 80a) integrally formed with the body portion 84 and extending into the interior cavity 82 of the protective tip 78, with each configured to be received by one of the eyes 90, 90a of the catheter 92. As in the insert of FIGS. 5-7, the interior cavity 82 of the protective tip 78 may be provided with one or more guide or spacer formations that help to properly orient the projection(s) 80, 80a with respect to the eye(s) 90, 90a of the catheter 92.

Figure 12A:
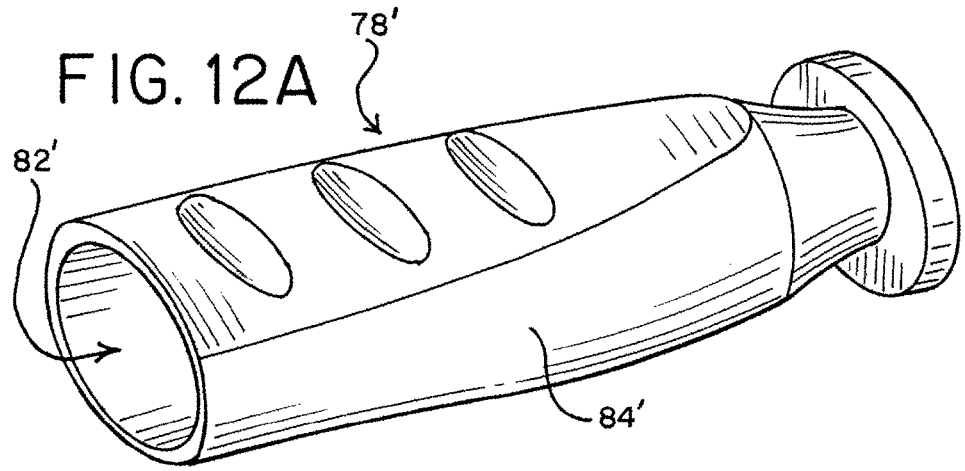
FIG. 12A is a perspective view of another embodiment of a protective catheter tip configured for use in a sleeveless urinary catheter assembly.
Figure 14A:
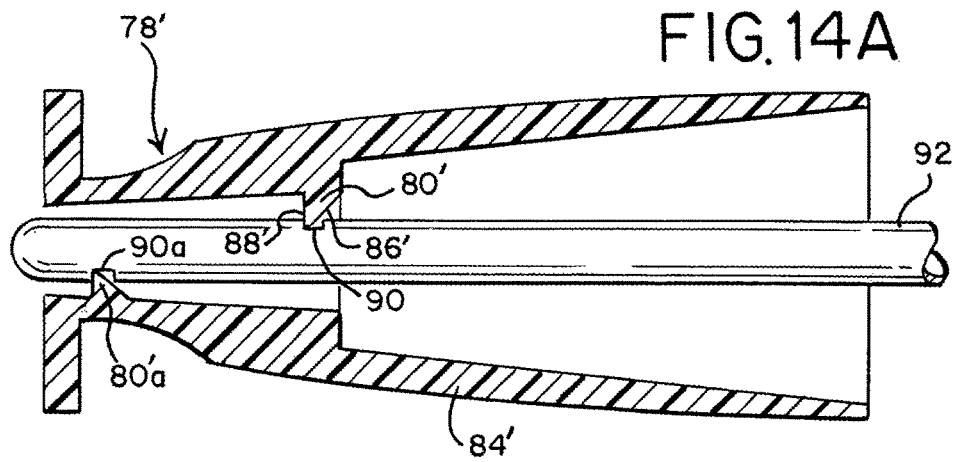
FIG. 14A is a cross-sectional view of the protective tip of FIG. 12A, showing a catheter positioned within the protective tip.

FIGS. 12A and 14A illustrate an alternative embodiment of the protective tip 78 of FIGS. 12-14, in which a "gripper-type" protective tip 78' is provided. As in the embodiment of FIGS. 12-14, the protective tip 78' of FIGS. 12A and 14A includes at least one projection 80' extending into the interior cavity 82' defined by the generally tubular body portion 84' of the protective tip 78'. The projection 80' may be configured according to the description of the projection 28 of FIG. 5, with an inclined surface 86' and a radial surface 88' configured to be at least partially positioned within an eye 90 of a urinary catheter 92 which is at least partially positioned within the body portion 84' (FIG. 14A). In the embodiment of FIGS. 12A and 14A, there are two projections (a distal projection 80' and a proximal projection 80'a) integrally formed with the body portion 84' and extending into the interior cavity 82' of the protective tip 78', with each configured to be received by one of the eyes 90, 90a of the catheter 92.

It is also within the scope of the present disclosure for the protective tip to include only one projection. For example, FIGS. 15-20 show a protective tip 94 having only one projection 96 that is integrally formed with the body portion 98 of the protective tip 94 and configured to be at least partially received by an eye of a urinary catheter positioned within the protective tip 94. In the embodiment of FIGS. 15-20, the body portion 98 of the protective tip 94 includes a slot 100 aligned with and positioned proximally of the projection 96. If provided, such a slot 100 may simplify the manufacture of the protective tip 94 if it is formed in an injection molding procedure, as the slot 100 represents the location of an insert or element positioned within the mold cavity to define the radial surface 102 of the projection 96.

It is also within the scope of the present disclosure for the protective tip itself to have a multiple-piece construction, rather than being provided as a single, unitary piece. For example, FIGS. 21A-22D show an embodiment of a two-piece protective tip 104 according to an aspect of the present disclosure. The illustrated protective tip 104 includes a proximal piece or member 106 and a distal piece or member 108, with the two pieces 106 and 108 being detachably connected. As best seen in FIGS. 22A-22D, the protective tip 104 includes at least one projection 110 extending into the interior cavity 112 defined by the generally tubular body portion of the protective tip 104. In the illustrated embodiment, two projections 110 and 110a are provided and are configured according to the description of the projection 28 of FIG. 5, with an inclined surface and a radial surface configured to be at least partially positioned within an eye 114, 114a of a urinary catheter 116 at least partially positioned within the body portion. In the illustrated embodiment, the projections 110 and 110a extend from the proximal piece 106, while there are no projections associated with the distal piece 108, but it is also within the scope of the present disclosure for the distal piece to also include one or more projections (e.g., comparable to the insert 56 and projections 58 of FIG. 10). It is also within the scope of the present disclosure for a two-piece protective tip to be provided without projections and to be associated with a catheter by any other suitable means.

It will be seen that the proximal piece 106 is comparable to the "introducer tip-type" protective tip 78 of FIGS. 12-14, while the distal piece 108 is comparable to the "gripper-type" protective tip 78' of FIGS. 12A and 14A. More particularly, the illustrated proximal piece 106 has a generally tubular body portion 118 that cooperates with the distal piece 108 to define the interior cavity 112 that extends, in part, between an open distal end 120 and a proximal access end 122 of the proximal piece 106. As in other "introducer tip-type" protective tips described herein, the open end 120 is the end of the proximal piece 106 into which the catheter 116 is inserted (in a direction toward the access end 122). The access end 122 is movable between a generally closed condition when the proximal end of the catheter 116 is positioned within the protective tip 104 and a generally open condition when the catheter 116 is advanced proximally (i.e., in a left-to-right direction in the orientation of FIGS. 21A-21D or the upward direction in the orientation of FIGS. 22A-22D) so as to pass through the access end 122 for advancement into and through the urethra. As shown, the access end 122 of the proximal piece 106 may include one or more slits 124 that allow it to move between the generally closed and generally open conditions.

As for the distal piece 108, it substantially encircles at least a portion of the proximal end of the catheter 116, but does not have a closed access end. Instead, the distal piece 108 has a generally tubular body portion 126 extending between open distal and proximal ends 128 and 130 and combining with the proximal piece 106 to define the interior cavity 112 of the protective tip 104. The distal open end 128 is the end of the distal piece 108 (and the protective tip 104) into which the catheter 116 is inserted (in a direction toward the proximal piece 106). As in the "gripper-type" protective tips described above, the proximal open end 130 is not movable into a closed condition, but remains open during use, thereby allowing the distal piece 108 to serve as a gripper or gripping member that may be held by a user to manipulate and deploy the catheter 116 without directly handling the catheter 116. The distal piece 108 may include one or more molded or formed portions, such as the illustrated oval-shaped formations (FIGS. 21A-21D), for improved gripping and handling of the distal piece 108.

The distal end 120 of the proximal piece 106 and the proximal end 130 of the distal piece 108 include features or formations 132 and 134 (FIGS. 22A-22D), respectively, configured to mate with each other to detachably secure the pieces 106 and 108 of the protective tip 104 together. In the illustrated embodiment, the formation of the distal end 120 of the proximal piece 106 is an outwardly facing, generally annular rib 132. The rib 132 of the proximal piece 106 is configured to be received within an inwardly facing, generally annular channel or groove 134 that comprises the formation of the distal piece 108. One or both pieces 106, 108 may be relatively rigid, but sufficiently flexible that, upon distal movement of the distal piece 108 with respect to the proximal piece 106 (FIGS. 21B, 21C, 22B, and 22D), one or both pieces 106, 108 deform to allow the rib 132 to unseat from the groove 134, thereby separating the two pieces 106 and 108. In one preferred embodiment, one or both of the pieces 106 and 108 (typically the distal piece 108) may be squeezed by a user to deform it, thereby unseating the rib 132 from the groove 134 prior to moving the distal piece 108 distally to separate it from the proximal piece 106. It should be understood that the illustrated embodiment is merely exemplary and that other means for detachably connecting the proximal and distal pieces of a two-piece protective tip (e.g., mating screw threads or a separate connector) may also be employed without departing from the scope of the present disclosure.

When the distal piece 108 has been fully separated from the proximal piece 106, the distal piece 108 may be moved proximally and distally (FIGS. 21D and 22D), thereby permitting a user to manipulate the catheter 116 without directly contacting (and potentially contaminating) it. If desirable, the two-piece protective tip 104 may be configured to allow for the two pieces 106 and 108 to be reconnected after being disconnected, as in the illustrated embodiment. In other embodiments, the connection between the two pieces may be frangible or otherwise irreversible, thereby preventing reconnection of the two pieces after they have been disconnected.

FIGS. 23A-23C illustrate another embodiment of a two-piece protective tip 200 according to an aspect of the present disclosure. The illustrated protective tip 200 may be configured according to the above description of the two-piece protective tip 104 of FIGS. 21A-22D, with a proximal piece 202 removably or detachably secured to a distal piece 204. As in the embodiment of FIGS. 21A-22D, the proximal piece 202 may be comparable to the "introducer tip-type" protective tip 78 of FIGS. 12-14, while the distal piece 204 is comparable to the "gripper-type" protective tip 78' of FIGS. 12A and 14A. The two pieces 202 and 204 may be detachably connected together at the distal end of the proximal piece 202 and the proximal end of the distal piece 204 according to the rib-and-groove arrangement described above with respect to the protective tip 104 of FIGS. 21A-22D or by any other suitable detachable connection arrangement.

In one embodiment, the protective tip 200 differs from the protective tip 104 of FIGS. 21A-22D by omitting an internal projection for receipt within an eye 206 of the associated catheter 208, but instead relies upon an access end 210 (of the type described above in greater detail) of the proximal piece 202 to engage the outer surface of the catheter 208 and hold the protective tip 200 in place on the catheter 208, while also allowing the protective tip 200 to be moved along the length of the catheter 208. However, it is also within the scope of the present disclosure for the tip 200 to be provided with one or more internal projections of the type described above or to be associated with the catheter 208 by any other suitable means.

Also in contrast to the embodiment of FIGS. 21A-22D, the protective tip 200 of FIGS. 23A-23C is not positioned at the proximal end of the catheter 208 prior to use, but is instead positioned at a distal end of the catheter 208, associated with a connecting member or funnel 212 at the distal end prior to use (e.g., while the protective tip 200 and catheter 208 are in a sterile package or container or wrapper), as shown in FIG. 23A. The funnel 212 may be provided according to conventional design for fluidly connecting the catheter 208 to a collection container, such as a collection bag into which urine drains. Preferably, the funnel 212 and/or an interior portion of the distal piece 204 include molded or formed contours or features that allow for the funnel 212 to detachably engage the distal piece 204 and the protective tip 200 prior to use. For example, the funnel 212 and the distal piece 204 may be configured such that there is a friction or interference fit therebetween that holds the protective tip 200 in place on the funnel 212 prior to use. In other embodiments, the protective tip 200 may be associated to the funnel 212 by a frangible connection or by a separate connector or fastener.

When a user is ready to use the catheter 208, it is removed from the packaging and the protective tip 200 is detached from the funnel 212. The manner in which the protective tip 200 is removed from the funnel 212 may vary depending on the mechanism by which the two are connected. In various exemplary embodiments, the protective tip 200 may be detached from the funnel 212 by rotating the protective tip 200 with respect to the funnel and/or by holding the funnel 212 in one hand and the protective tip 200 in the other while moving the protective tip 200 in a proximal relative direction with respect to the funnel 212.

With the protective tip 200 fully detached from the funnel 212, the protective tip 200 may be slid along the catheter 208 in a proximal direction, as shown in FIG. 23B. The protective tip 200 is advanced proximally along the catheter 208 until the access end 210 at the proximal end of the protective tip 200 clears the proximal end of the catheter 208 and moves from an open condition (with the catheter 208 extending therethrough, as in FIGS. 23A and 23B) to a closed condition, as shown in FIG. 23C. When the protective tip 200 is in this position, the distal piece 204 may be detached from the proximal piece 202 according to the method described above in greater detail with respect to the embodiment of FIGS. 21A-22D or according to any other suitable means.

Finally, when the two pieces 202 and 204 of the protective tip 200 are separated from each other, the distal piece 204 may be moved proximally and distally (FIG. 23C), thereby permitting a user to manipulate the catheter 208 without directly contacting (and potentially contaminating) it. The two-piece protective tip 200 may be configured to allow for the two pieces 202 and 204 to be reconnected after being disconnected, such as by pressing them distally until the distal piece 204 engages the funnel 212 and the distal end of the proximal piece 202 reconnects to the proximal end of the distal piece 204 (i.e., by returning the catheter 208 and protective tip 200 to the initial condition of FIG. 23A). In other embodiments, the connection between the two pieces may be frangible or otherwise irreversible, thereby preventing reconnection of the two pieces after they have been disconnected.

FIGS. 24A-24C illustrate another embodiment of a two-piece protective tip according to an aspect of the present disclosure. The illustrated protective tip may be configured generally according to the above description of the two-piece protective tip 104 of FIGS. 21A-22D, with a proximal piece 300 that is comparable to the "introducer tip-type" protective tip 78 of FIGS. 12-14, while the distal piece 302 is comparable to the "gripper-type" protective tip 78' of FIGS. 12A and 14A. In the illustrated embodiment, the proximal piece 300 includes at least one internal projection 304 received by an eye 306 of the catheter 308 (as described above in greater detail with respect to the embodiment of FIGS. 12-14), while the distal piece 302 omits such an internal projection. In other embodiments, the proximal piece 300 may include any other suitable means for movably securing it in place at a proximal end of the catheter 308.

In contrast to the embodiment of FIGS. 23A-23C, only the distal piece 302 of the protective tip is initially positioned at the distal end of the catheter 308 and detachably connected to a funnel 310 at the distal end prior to use, as shown in FIGS. 24A and 24B. While the distal piece 302 is initially connected to the funnel 310, the proximal piece 300 is initially detachably connected to the proximal end of the catheter 308 (as in the embodiment of FIGS. 12-14) while the protective tip and catheter 308 are in a sterile package or container or wrapper. As described above with respect to the embodiment of FIGS. 23A-23C, the funnel 310 and/or an interior portion of the distal piece 302 preferably include molded or formed contours or features that allow for the funnel 310 to detachably engage the distal piece 302 prior to use.

When a user is ready to use the catheter 308, it is removed from the packaging and the distal piece 302 of the protective tip is detached from the funnel 310. The manner in which the distal piece 302 is removed from the funnel 310 may vary depending on the mechanism by which the two are connected. In various exemplary embodiments, the distal piece 302 may be detached from the funnel 310 by rotating the distal piece 302 with respect to the funnel and/or by holding the funnel 310 in one hand and the distal piece 302 in the other while moving the distal piece 302 in a proximal relative direction with respect to the funnel 310.

With the distal piece 302 of the protective tip fully detached from the funnel 310, the distal piece 302 may be moved proximally and distally (FIG. 24C), thereby permitting a user to manipulate the catheter 308 without directly contacting (and potentially contaminating) it. After use, the distal piece 302 may be moved distally along the catheter 308 to reengage the funnel 310 for disposal of the catheter 308. In other embodiments, the connection between the distal piece 302 and the funnel 310 may be frangible or otherwise irreversible, thereby preventing reconnection of the distal piece 302 and the funnel 310 after they have been disconnected.

FIGS. 25A-25C illustrate another embodiment of a two-piece protective tip according to an aspect of the present disclosure. The illustrated protective tip may be configured generally according to the above description of the two-piece protective tip of FIGS. 24A-24C, with a proximal piece 400 that is comparable to the "introducer tip-type" protective tip 78 of FIGS. 12-14 and a distal piece 402 that is comparable to the "gripper-type" protective tip 78' of FIGS. 12A and 14A. In the illustrated embodiment, the proximal piece 400 includes at least one internal projection 404 received by an eye 406 of the catheter 408, while the distal piece 302 omits such an internal projection. In other embodiments, the proximal piece 400 may include any other suitable means for movably securing it in place at a proximal end of the catheter 408.

As in the embodiment of FIGS. 24A-24C, the proximal piece 400 of the protective tip is initially detachably connected to the proximal end of the catheter 408 prior to use (e.g., while the protective tip and catheter 408 are in a sterile package or container or wrapper). However, in contrast to the embodiment of FIGS. 24A-24C, the distal piece 402 is initially positioned at a midsection or intermediate portion of the catheter 408, between the proximal piece 400 and the funnel 410 at the distal end of the catheter 408, rather than being detachably connected to the funnel 410. The distal piece 402 may be fully separate from the catheter 408 or have an internal projection or formation configured to engage the outer surface of the catheter 408, such as a projection of the type described above in greater detail with respect to the embodiment of FIG. 10.

When a user is ready to use the catheter 408, it is removed from the packaging and the distal piece 402 may be moved proximally (FIG. 25B) and distally (FIG. 25C), thereby permitting a user to manipulate the catheter 408 without directly contacting (and potentially contaminating) it.

FIGS. 26A and 26B show yet another embodiment of a two-piece protective tip 500 according to an aspect of the present disclosure. The illustrated protective tip 500 includes a proximal piece or member 502 and a distal piece or member 504. The proximal piece 502 may be comparable to the "introducer tip-type" protective tip 78 of FIGS. 12-14, with one or more internal projections that are received within eyes at the proximal end of the catheter 506 to detachably secure the proximal piece 502 to the proximal end of the catheter 506. It is also within the scope of the present disclosure for the proximal piece 502 of the protective tip 500 to be detachably secured to the proximal end of the catheter 506 by any other suitable means.

As for the distal piece 504, it comprises a relatively short sleeve with a fixed portion 508 and a free portion 510. In one embodiment, the distal piece 504 is formed from one or more thin, flexible sheets of material, such as a polymeric material (e.g., polyethylene) or the like. The fixed portion 508 is secured to the proximal piece 502 by any suitable means, which may vary depending on the configuration and material composition of the proximal and distal pieces 502 and 504. In one embodiment, the fixed portion 508 is secured to the proximal piece 502 by a heat seal, but other means (e.g., adhesive or mechanical fasteners) may also be employed without departing from the scope of the present disclosure. The free portion 510 encircles a portion of the catheter 506 without being secured thereto.

The distal piece 504 is relatively short compared to the length of the catheter 506, such that the distal piece 504 extends only partially along the length of the catheter 506. Preferably, the free portion 510 is sufficiently elongated that it may be gripped by a user for manipulating the catheter 506, without being overly elongated. For example, the distal piece 504 may be configured such that its overall length is approximately four inches, with the free portion 510 being between two and three inches long. In other embodiments, the length of the distal piece 504 and the free portion 510 may vary without departing from the scope of the present disclosure.

The fixed and free portions 508 and 510 of the distal piece 504 have a frangible portion 512 therebetween that may be torn or broken or severed to separate the fixed and free portions 508 and 510. The frangible portion 512 may be variously configured without departing from the scope of the present disclosure, but in the illustrated embodiment, the frangible portion 512 may comprise a line of perforations that may be torn or broken or severed to separate the fixed and free portions 508 and 510 of the distal piece 504.

In use, the proximal piece 502 and/or the fixed portion 508 of the distal piece 504 are gripped with one hand, while the free portion 510 of the distal piece 504 is gripped with the other hand. The user then moves the free portion 510 in a distal direction relative to the proximal piece 502 until the frangible portion 512 tears or breaks to separate the free portion 510 of the distal piece 504 from the fixed portion 508. When the free portion 510 has been fully separated from the proximal piece 502 (and from the fixed portion 508 of the distal piece 504), the free portion 510 may be moved proximally and distally (FIG. 26B), thereby permitting a user to manipulate the catheter 506 without directly contacting (and potentially contaminating) it.

FIGS. 27-31 illustrate another embodiment of a sleeveless urinary catheter assembly 600 according to the present disclosure. In contrast to the other embodiments described herein, the sleeveless urinary catheter assembly 600 incorporates a modified catheter 602. The illustrated catheter 602 comprises a catheter body 604 that may be provided generally according to the convention design (e.g., extending between proximal and distal end sections, with one or more eyes 606 at or adjacent to the proximal end section 608 and a funnel or the like at the distal end section). Associated with the proximal end section 608 of the catheter body 604 is an extension 610 comprising a necked-down section 612 and a proximal or enlarged end 614. Although the proximal end 614 of the extension 610 may be referred to as an "enlarged" end, it is preferably enlarged only with respect to the necked-down section 612 (as will be described in greater detail below) and has a maximum outer diameter that is no greater than the maximum outer diameter of the catheter body 604. Furthermore, it may also be preferred for the extension 610 to be generally coaxial with the catheter body 604, as these two design features may provide improved comfort of a user of the sleeveless urinary catheter assembly 600.

Depending on the nature of the catheter body 604 and the extension 610 (e.g., their material compositions and shapes), the manner by which the extension 610 is secured to the catheter body 604 may vary without departing from the scope of the present disclosure. In one embodiment, the extension 610 and the catheter body 604 are manufactured from similar materials (e.g., polymer materials), with the extension 610 being more flexible than the catheter body 604 (e.g., by being manufactured from a material having a lower durometer hardness, and/or a lower modulus of elasticity). The material composition of the extension 610 may vary without departing from the scope of the present disclosure, but it may be preferred for the extension 610 to be manufactured so as to feel and perform similarly to a conventional catheter during use. It should also be understood that the catheter body 604 and the extension 610 are not necessarily provided separately, but the extension 610 may be integrally formed as a proximal end of the catheter body 604 having an enlarged section.

The illustrated necked-down portion 612 is shown as having a generally cylindrical or frusto-conical shape, while the proximal end 614 has a generally spherical or bulb shape, with a proximal region of the necked-down portion 612 tapering outwardly to smoothly transition to a distal region of the proximal end 614. However, other configurations may be employed without departing from the scope of the present disclosure. As noted above, it is preferred for at least a portion of the necked-down section 612 to have a diameter that is less than the maximum diameter of the proximal end 614 of the extension 610 (as in the illustrated embodiment) in order to retain at least a portion of the extension 610 within a protective tip 616, as will be described in greater detail below.

Turning now to the protective tip 616 of the sleeveless urinary catheter assembly 600, it includes an outer member or piece 618 and an inner member or piece or insert 620. In the illustrated embodiment, the outer member 618 is configured similarly to an "introducer tip-type" protective tip of the type shown in FIGS. 2 and 3. In other embodiments, the outer member 618 may be provided as a "gripper-type" protective tip of the type shown in FIGS. 2A and 3A or in any other suitable configuration.

Figure 28:
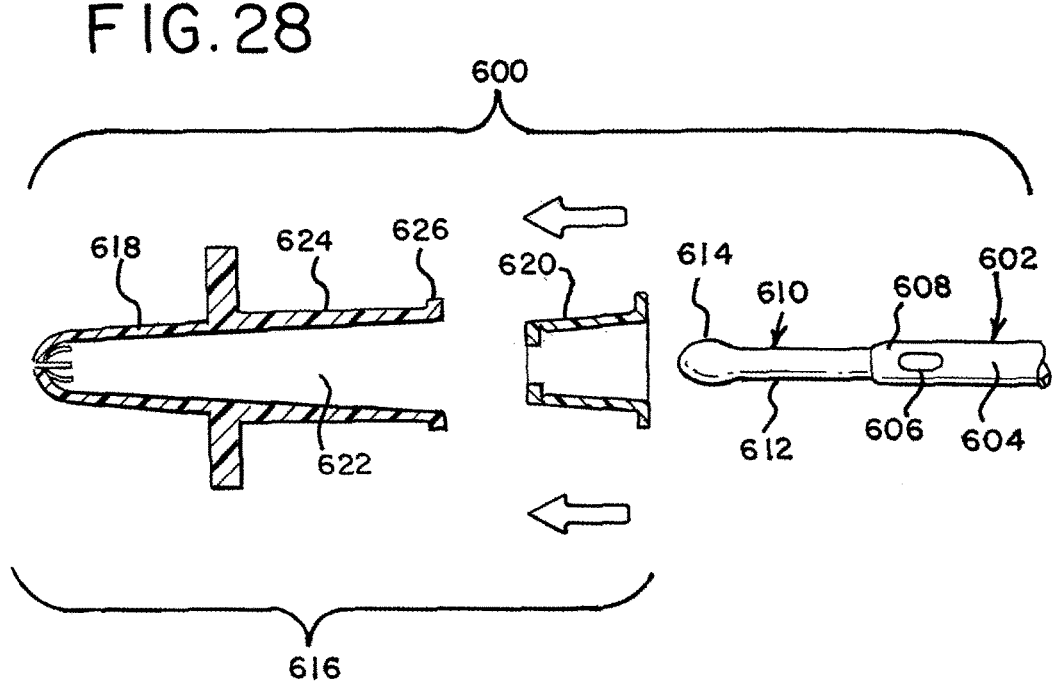
FIG. 28 is a cross-sectional, exploded view of the protective tip and urinary catheter of FIG. 27.

The insert 620 is configured to be at least partially received within an interior cavity 622 defined by a generally tubular body portion 624 of the outer member 618 that extends between proximal and distal end sections of the outer member 618. The distal open end 626 is the end of the outer member 618 into which the insert 620 is inserted, in a direction toward the proximal end, as shown in FIG. 28. In the illustrated embodiment, the insert 620 is secured to the distal end 626 of the outer member 618, with a small portion of the insert 620 extending outside of the cavity 622 to properly orient the insert 620 and prevent over-insertion thereof into the outer member 618. However, in other embodiments, the insert 620 may be secured to any other interior region of the body portion 624 of the outer member 618 to be either fully or partially received within the cavity 622. In one embodiment, the insert 620 may be secured within the outer member 618 by a friction fit or interference fit when positioned within the outer member 618 and/or it may be held in place by an adhesive or the like. In other embodiments, other means may be provided for associating the insert 620 to the outer member 618.

The exact structure of an exemplary insert 620 is shown in greater detail in FIGS. 29-31. In the illustrated embodiment, the insert 620 includes a body portion 628 configured to be secured to the outer member 618. The configuration of the body portion 628 is preferably complementary to the shape of the portion of the outer member 618 to which it is to be secured. For example, in the illustrated embodiment, the body portion 628 of the insert 620 is generally tubular to match the shape of the generally tubular body portion 624 of the outer member 618 to which it is secured. However, the shape of the body portion 628 may vary without departing from the scope of the present disclosure.

Associated with the body portion 628 of the insert 620 is a projection 630. The projection 630 extends generally radially inwardly and may be variously configured. For example, the projection 630 may be generally annular or comprise a plurality of inwardly extending "fingers" or segments. Regardless of the exact shape of the projection 630, it defines an opening or aperture 632 through which the necked-down section 612 of the extension 610 extends, as shown in FIGS. 29-31. The diameter of the opening 632 is smaller than a maximum diameter of the proximal end 614 of the catheter extension 610, but may be comparable to the diameter of the necked-down section 612, as in FIG. 29, or it may be larger or smaller than the diameter of the necked-down section 612. In a preferred embodiment, the projection 630 is hingedly or pivotally connected to the body portion 628 of the insert 620, such that the orientation of the projection 630 may vary to effectively change the diameter of the opening 632. In the illustrated embodiment, the insert 620 includes an integrally formed hinge 634 positioned adjacent to the projection 630. The illustrated hinge 634 is a relatively narrow proximal end section of the body portion 628, which provides increased flexibility on account of being relatively narrow. While the illustrated insert 620 includes an integrally formed projection 630 and hinge 634, it is within the scope of the present disclosure for either or both of these components to be separately provided.

By providing a hinge 634 or comparable structure, the projection 630 may pivot or rotate with respect to the remainder of the insert 620. For example, FIG. 29 shows the projection 630 in a neutral or un-pivoted orientation. FIG. 30 shows the projection 630 pivoting or rotating in one direction, while FIG. 31 shows the projection 630 pivoting or rotating in an opposite direction. When the projection 630 pivots toward the hinge 634 (as in FIG. 30), the projection 630 may come into contact with the hinge 634 or some other part of the insert 620 to limit its pivotal movement in that direction. When the projection 630 pivots away from the hinge 634 (as in FIG. 31), the projection 630 may come into contact with a portion of the outer member 618 to limit its pivotal movement in that direction. The material composition of the projection 630 may also or alternatively limit the pivotal movement of the projection 630 in either direction.

FIG. 28 shows the catheter 602 initially separate from the protective tip 616 prior to assembly. The catheter 602 is associated to the protective tip 616 by relative movement of the catheter 602 toward insert 620 (i.e., in a right-to-left direction in the orientation of FIG. 28), with the extension 610 facing the insert 620. Alternatively, the catheter body 604 may be pulled through the insert 620 (in a left-to-right direction in the orientation of FIG. 28) to arrive at the configuration of FIGS. 27 and 29, in which the necked-down portion 612 of the catheter extension 610 is received by the opening 632 of the insert 620, with the proximal end 614 and catheter body 604 on opposite sides of the projection 630. The catheter 602 may be so associated to the insert 620 prior to or after the insert 620 has been associated to the outer member 618 or at substantially the same time.

Figure 27:
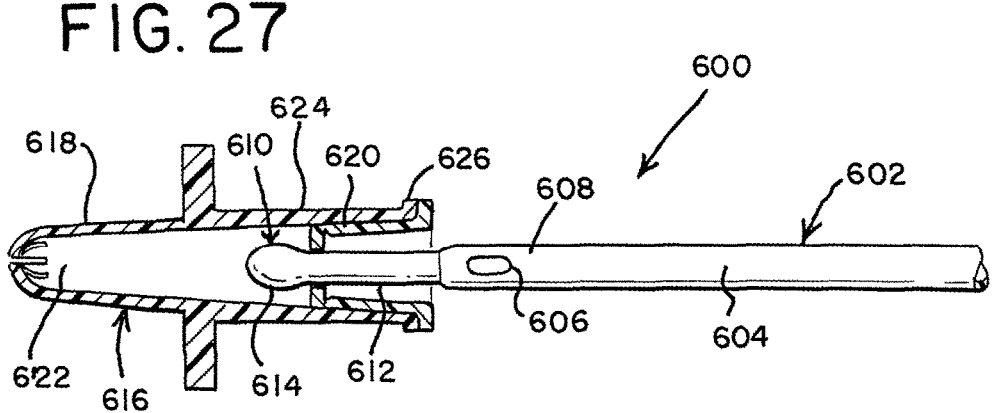
FIG. 27 is a cross-sectional view of a protective tip provided in combination with a modified urinary catheter.

With the sleeveless urinary catheter assembly 600 in the configuration of FIG. 27, it is ready for handling and use. Prior to introduction of the catheter 602 into the urethra, the insert 620 prevents the catheter 602 from being retracted or withdrawn from the protective tip 616. More particularly, FIG. 30 shows the catheter extension 610 being moved in a distal direction wherein the proximal end 614 of the catheter extension 610 comes into contact with the projection 630 of the insert 620, on account of the proximal end 614 having a larger diameter than the opening 632 of the insert 620. Continued distal movement of the catheter extension 610 may pivot the projection 630 about the hinge 634 to some degree, but the projection 630 is eventually prevented from further rotational or pivotal movement (as described above). When the pivotal movement of the projection 630 has ceased, further distal movement of the catheter extension 610 is prevented by interference between the projection 630 and the proximal end 614 of the catheter extension 610, thereby retaining the catheter extension 610 within the protective tip 616 and maintaining sterility prior to use. While FIG. 30 shows only the catheter extension 610 positioned and retained within the protective tip 616, it is within the scope of the present disclosure for some portion of the catheter body 604 to also be positioned and retained within the protective tip 616 prior to use.

When the catheter 602 is to be inserted into the urethra, it is moved proximally with respect to the protective tip 616 (i.e., in the right-to-left direction in the orientation of FIG. 27). FIG. 31 shows how the projection 630 of the insert 620 allows unrestricted proximal relative movement of the catheter extension 610, on account of the necked-down section 612 of the catheter extension 610 (as well as the catheter body 604) having a smaller diameter than the opening 632 defined by the projection 630 when the projection 630 pivots away from the hinge 634. When it is desired to withdraw the catheter 602 from the urethra, it may be moved distally with respect to the protective tip 616 until the proximal end 614 of the catheter extension 610 engages and is retained by the projection 630, as shown in FIG. 30.

Figure 32:
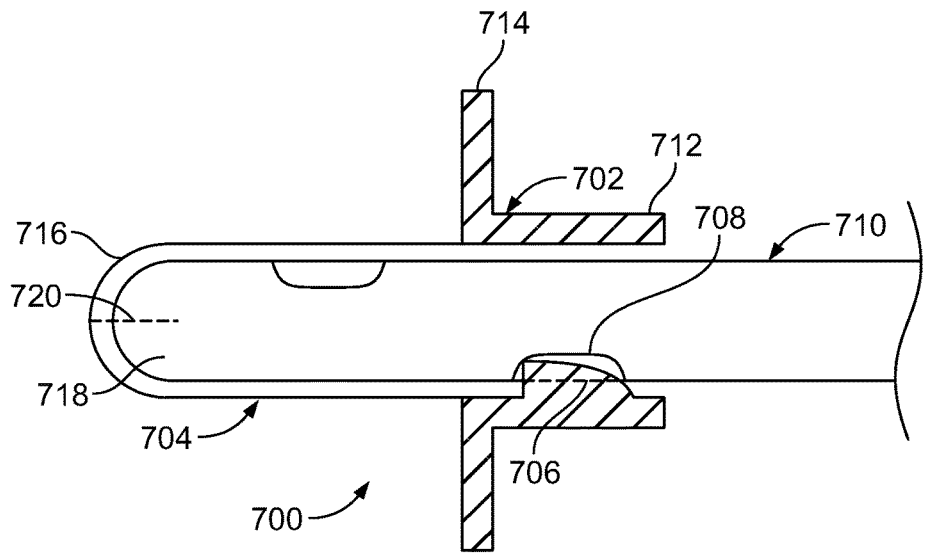
FIG. 32 is a side elevational view of a two-piece protective tip, with selected portions of the protective tip broken away for illustrative purposes.
Figure 33:
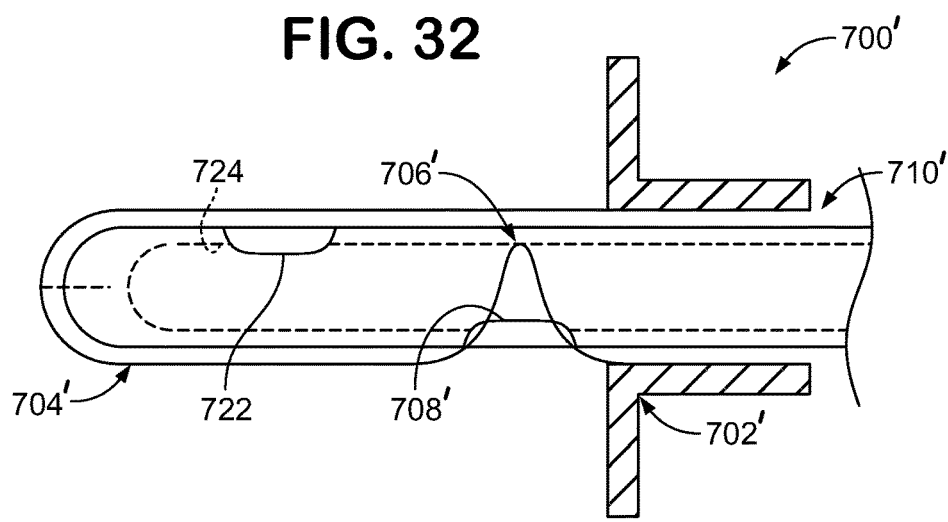
FIG. 33 is a side elevational view of another embodiment of a two-piece protective tip, with selected portions of the protective tip broken away for illustrative purposes.

FIG. 32 illustrates another embodiment of a protective tip 700 according to an aspect of the present disclosure. The illustrated protective tip 700 is provided as a single component, but includes distal and proximal portions or pieces 702 and 704 formed of different materials, which are secured together. The protective tip 700 includes at least one projection 706 extending into the interior cavity defined by the generally tubular body portion of the protective tip 700. In the illustrated embodiment, one projection 706 is provided and may be configured according to the description of the projection 28 of FIG. 5, with an inclined surface and a radial surface configured to be at least partially positioned within an eye 708 of a urinary catheter 710 at least partially positioned within the body portion. In the illustrated embodiment, the projection 706 extends from the distal piece 702, while there are no projections associated with the proximal piece 704, but it is also within the scope of the present disclosure for the proximal piece 704 to also include one or more projections (as shown in the embodiment of FIG. 33, as will be described in greater detail herein).

The distal piece 702 may be similarly configured to the distal section of the protective tip 94 of FIGS. 15-20, with a tubular body or barrel 712 associated with the distal face of a generally annular flange 714 having a larger outer diameter than the tubular barrel 712. The distal piece 702 may be a molded component, which is formed of a generally rigid material, a generally flexible or resilient material, or a material having intermediate rigidity. It may be preferred for the distal piece 702 to have a greater rigidity or stiffness than the proximal piece 704.

As for the proximal piece 704, it is shaped similarly to the proximal section of the protective tip 94 of FIGS. 15-20, extending from a proximal face of the flange 714 and having an outer diameter sized to fit within a urethra. The proximal end 716 of the proximal piece 704 is provided in an initially closed condition to enclose the proximal end portion 718 of an associated urinary catheter 710. The proximal piece 704 of the protective tip 700 is preferably formed of a relatively thin material having a high moisture vapor transmission rate (e.g., polyurethane) to ensure that the proximal end portion 718 of the urinary catheter 710 is adequately hydrated. Preferably, the material of the proximal piece 704 is inherently lubricious, but it is also within the scope of the present disclosure for the material of the proximal piece 704 to be non-lubricious, in which case a lubricant may be applied to the proximal piece 704 prior to advancement into a urethra. Typically, a proximal piece 704 formed of a thin film will have a smaller outer diameter than the proximal sections of the protective tips described above, in which case the protective tip 704 may be less intimidating to a user. While only the embodiments of FIGS. 32 and 33 are illustrated as having thin film proximal sections, it should be understood that the other protective tips described herein may be provided with proximal sections formed of a thin film material. Protective tips having a proximal end or piece formed of a thin film material (which may be referred to as "protective sleeve tips") are described in greater detail in PCT Patent Application Publication No. WO 2013/130459 A1, which is incorporated herein by reference.

In a protective tip 700 having a proximal piece 704 formed of a thin film, the proximal end 716 of the proximal piece 704 is configured to move only from the closed condition of FIG. 32 to an open condition, in contrast to the other protective tips described herein, which have proximal ends that are configured to move between open and closed conditions. The proximal end 716 of the proximal piece 704 may include a weakened section 720 that is rupturable or frangible or capable of being manipulated to move it from the closed condition to the open condition. For example, the proximal end 720 may include a sealed opening or slit or aperture or one or more perforations that is configured to yield to a urinary catheter 710 moved proximally within the interior cavity of the protective tip 700. Upon sufficient relative proximal movement, the proximal end portion 718 of the urinary catheter 710 presses against the proximal end 716 of the proximal piece 704 and unseals or ruptures or breaks or otherwise irreversibly moves the weakened section 720 from the closed condition to an open condition. Typically, this occurs after the proximal piece 704 has been advanced into a urethra until the flange 714 prevents further proximal advancement. The urinary catheter 710 is then moved proximally with respect to the protective tip 700 (which requires moving the projection 706 out of the catheter eye 708) to pass through the weakened section 720 of the proximal end 716 (by moving the weakened section 720 to the open condition), thereby passing into the urethra without being exposed to the outside environment.

The proximal piece 704 may be secured to the distal piece 702 at any of a number of suitable locations, such as to the proximal face of the flange 714 or to the inner surface of the barrel 712 of the distal piece 702. In another embodiment, the proximal piece 704 may be secured to the distal end of the distal piece 702 and extend proximally through the interior of the distal piece 702. The distal and proximal pieces 702 and 704 may be secured together by any suitable means, which may vary depending on the material compositions of the distal and proximal pieces 702 and 704.

As mentioned above, FIG. 33 illustrates a variation of the protective tip 700 of FIG. 32. The protective tip 700' of FIG. 33 includes a distal portion or piece 702' secured to a proximal portion or piece 704', as in the embodiment of FIG. 32. In contrast to the embodiment of FIG. 32, the distal piece 702' of the protective tip 700' of FIG. 33 omits a projection, and may instead have a generally smooth or featureless inner surface. The projection 706' is instead associated with the proximal piece 704', extending into the interior cavity of the protective tip 700', where it is at least partially received within an eye 708' of an associated urinary catheter 710'. In the embodiment of FIG. 33, only one projection 706' is provided to be at least partially received within the distal catheter eye 708', but it is also within the scope of the present disclosure for a projection to instead be at least partially received within the proximal catheter eye 722. Additionally, the proximal piece 704' may include a pair of projections, with one projection being received in each catheter eye 708', 722, or the distal and proximal pieces 702' and 704' may each include one projection that is received in one of the catheter eyes 708', 722.

The projection 706' may be formed by pressing or otherwise advancing the film material overlaying the eye 708' inwardly into the hollow interior of the urinary catheter 710' through the eye 708'. The film material may then be secured to the inner surface 724 of the urinary catheter 710' to define the projection 706'. It may be advantageous for the film material of the proximal piece 704' to be weakly secured to the inner surface 724 of the urinary catheter 710', such that the film material is present within the eye 708' to provide a retention feature, without significantly resisting detachment from the urinary catheter 710' as the urinary catheter 710' is moved proximally with respect to the protective tip 700'. In one embodiment, the film material of the proximal piece 704' is secured to the inner surface 724 of the urinary catheter 710' by a peelable heat seal or tack weld or thermal bond. Preferably, the projection 706' is configured such that the seal between the projection 706' and the urinary catheter 710' will separate upon application of the standard force that a user would apply when advancing the urinary catheter 710' into the urethra. One method of creating such a seal involves the use of materials that have poor melt temperature compatibility and demonstrate poor adhesion once wet and sterilized, such as a DUREFLEX® U073 polyurethane film material from Bayer MaterialScience LLC of South Deerfield, Mass., and a polyvinyl chloride urinary catheter material.

Figure 34:
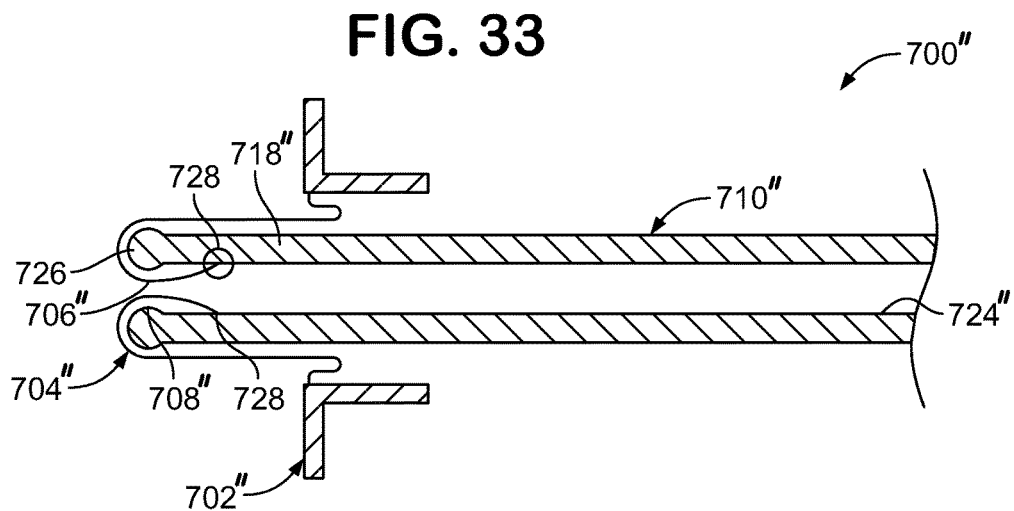
FIG. 34 is a cross-sectional view of a two-piece protective tip for use in combination with an open-ended urinary catheter.

FIG. 34 illustrates a sleeveless urinary catheter assembly that is a variation of the assembly shown in FIG. 33. The protective tip 700" of FIG. 34 includes a distal portion or piece 702" secured to a proximal portion or piece 704", as in the embodiment of FIG. 33. In contrast to the embodiment of FIG. 33, the associated urinary catheter 710" is open-ended, with an eye 708" positioned at the proximal end 726 of the urinary catheter 710", rather than being defined in a lateral wall of the proximal end portion 718". As in the embodiment of FIG. 33, the proximal piece 704" includes a projection 706" that extends into the interior cavity of the protective tip 700", where it is at least partially received within the eye 708" of the associated urinary catheter 710".

The projection 706" may be formed by pressing or otherwise advancing the film material at the proximal end of the proximal piece 704" distally into the hollow interior of the urinary catheter 710" through the eye 708". The film material may then be secured to the inner surface 724" of the urinary catheter 710" to define the projection 706". As in the embodiment of FIG. 33, it may be advantageous for the film material of the proximal piece 704" to be weakly secured to the inner surface 724" of the urinary catheter 710", such that the film material is present within the eye 708" to provide a retention feature, without significantly resisting detachment from the urinary catheter 710" as the urinary catheter 710" is moved proximally with respect to the protective tip 700". For example, the film material of the proximal piece 704" may be secured to the inner surface 724" of the urinary catheter 710" by a peelable heat seal or tack weld or thermal bond. Preferably, the projection 706" is configured such that the seal between the projection 706" and the urinary catheter 710" will separate upon application of the standard force that a user would apply when advancing the urinary catheter 710" into the urethra. As described above with respect to the embodiment of FIG. 33, one method of creating such a seal involves the use of materials that have poor melt temperature compatibility and demonstrate poor adhesion once wet and sterilized, such as a DUREFLEX® U073 polyurethane film material from Bayer MaterialScience LLC of South Deerfield, Mass., and a polyvinyl chloride urinary catheter material.

In the illustrated embodiment, an annular seal 728 is formed between the between the proximal piece 704" and the inner surface 724" of the urinary catheter 710" to form the projection 706". If the proximal piece 704" is formed of a tubular or open-ended material, then the eye 708" of the urinary catheter 710" will remain open (as shown in FIG. 34), whereas a projection formed by an annular seal will block and overlay the eye 708" if the proximal piece has a closed end. If the proximal piece has a closed end, it preferably includes a weakened section, as in the embodiments of FIGS. 32 and 33, to ensure that the urinary catheter 710" may be advanced proximally through the proximal piece during use. While FIG. 34 shows the projection 706" secured to the urinary catheter 710" by an annular seal 728, it is within the scope of the present disclosure for the projection 706" to be secured to the urinary catheter 710" by a non-annular seal, such as by sealing the film material to the urinary catheter 710" at only one or more locations along an inner perimeter of the urinary catheter 710", rather than sealing the film material along an entire inner perimeter.

Figure 35:
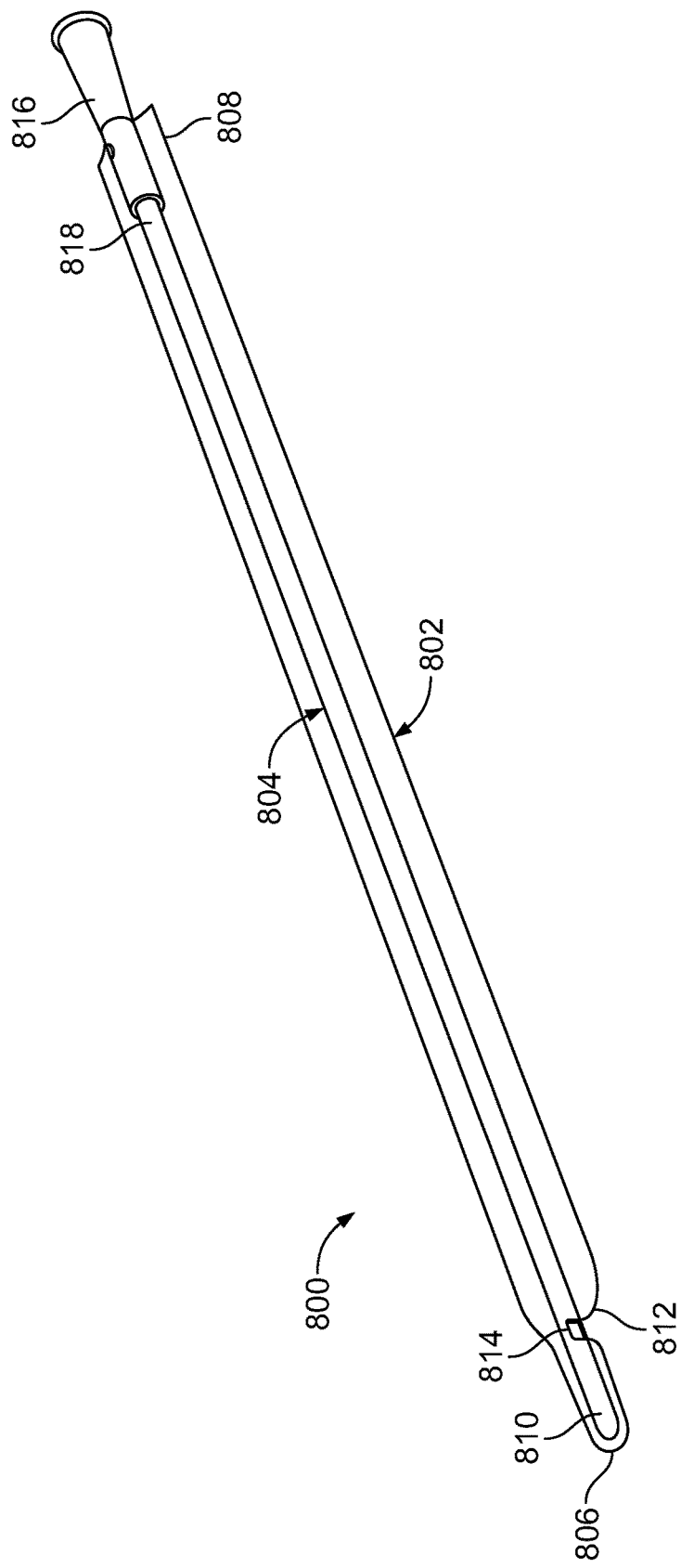
FIG. 35 is a perspective view of a urinary catheter assembly having a urinary catheter enclosed within a protective sleeve tip.

FIG. 35 illustrates a urinary catheter assembly 800 that may be understood as a variation of the one shown in FIG. 33. As described above in greater detail, the protective tip 700' of FIG. 33 has a two-piece construction, with a proximal protective sleeve tip 704' formed of a film material secured to a molded distal piece 702'. Compared to the protective tip 700' of FIG. 33, the embodiment of FIG. 35 eliminates the distal piece and extends and elongates the protective sleeve tip 802 to the extent that it covers and encloses the entire associated urinary catheter 804. More particularly, the illustrated protective tip or protective sleeve tip 802 extends between a closed proximal end 806 and an open distal end 808. As in the embodiments of FIGS. 32 and 33, the proximal end 806 of the protective sleeve tip 802 preferably includes a weakened section that is rupturable or frangible or capable of being manipulated to move it from the closed condition to an open condition, in which at least the proximal end portion 810 of the urinary catheter 804 may be proximally advanced. For example, the proximal end 806 of the protective sleeve tip 802 may include a sealed opening or slit or aperture or one or more perforations that is configured to yield when the urinary catheter 804 is moved proximally within the interior cavity of the protective sleeve tip 802. Upon sufficient relative proximal movement, the proximal end portion 810 of the urinary catheter 802 presses against the proximal end 806 of the protective sleeve tip 802 and unseals or ruptures or breaks or otherwise irreversibly moves the weakened section from the closed condition to an open condition.

The proximal end 806 of the protective sleeve tip 802 or a portion adjacent thereto may be formed with a projection 812 that extends into the interior cavity defined by the generally tubular body portion of the protective sleeve tip 802 to be at least partially received by an eye 814 of the urinary catheter 802. The projection 812 of the protective sleeve tip 802 of FIG. 35 may be formed and configured according to the above description of the projection 706' of FIG. 33, for example by pressing or otherwise advancing the film material overlaying the eye 814 inwardly into the hollow interior of the urinary catheter 804 through the eye 814 and then securing the film material to an inner surface of the urinary catheter 804 to define the projection 812. As in the embodiment of FIG. 33, it may be advantageous for the projection 812 to be weakly secured to the inner surface of the urinary catheter 804 (e.g., by a peelable heat seal or tack weld or thermal bond), such that the film material is present within the eye 814 to provide a retention feature, without significantly resisting detachment from the urinary catheter 804 as the urinary catheter 804 is moved proximally with respect to the protective sleeve tip 802. While FIG. 35 shows a protective sleeve tip 802 having only one projection 812, it is within the scope of the present disclosure for a protective sleeve tip to include a plurality of projections, such as a number of projections which is equal to the number of catheter eyes, with each catheter eye receiving one of the projections. Additionally, while FIG. 35 shows a protective sleeve tip 802 having a closed proximal end 806, with a projection 812 extending into a catheter eye 814 defined in a lateral wall of a urinary catheter 804, it should be understood that the protective sleeve tip 802 of FIG. 35 may be modified to include an open proximal end portion, with a projection that extends into a catheter eye at the proximal end of the proximal end portion of a urinary catheter, similar to the protective sleeve tip 704" of FIG. 34.

In the illustrated embodiment, the open distal end 808 of the protective sleeve tip 802 is secured to a connecting member or funnel 816 associated with the distal end portion 818 of the urinary catheter 804. Preferably, the open distal end 808 is sealed around an entire perimeter of the funnel 816 to fully shield the enclosed urinary catheter 804 from the outside environment. The urinary catheter 804 may be moved proximally with respect to the protective sleeve tip 802 by holding a portion of the protective sleeve tip 802 (e.g., a portion located between the proximal and distal ends 806 and 808) in place while gripping the funnel 816 and then moving the funnel 816 proximally. Alternatively, the funnel

816 may be held in place while gripping a portion of the protective sleeve tip 802 and moving the protective sleeve tip 802 distally. In another alternative, the funnel 816 may be moved proximally while simultaneously gripping and moving the protective sleeve tip 802 distally to unseat the projection 812 from the catheter eye 814 and move the proximal end portion 810 of the urinary catheter 804 into contact with the proximal end 806 of the protective sleeve tip 802, thereby moving the weakened section of the proximal end 806 to an open condition.

In an alternative embodiment, the open distal end 808 of the protective sleeve tip 802 may encircle the funnel 816 without being secured to the funnel 816. In this case, a user may grip the distal end 808 of the protective sleeve tip 802 and move it distally with respect to the urinary catheter 804 and funnel 816 to unseat the projection 812 from the catheter eye 814 and move the proximal end portion 810 of the urinary catheter 804 into contact with the proximal end 806 of the protective sleeve tip 802, thereby moving the weakened section of the proximal end 806 to an open condition. In this embodiment, it may be preferred for the opening of the open distal end 808 of the protective sleeve tip 802 to be comparable in size to a perimeter of the funnel 816 to ensure a tight or close fit between the protective sleeve tip 802 and the funnel 816, which better shields the urinary catheter 804 from the outside environment.

According to a method of using the urinary catheter assemblies described herein, the protective tip is held in one hand, with the funnel at the distal end of the catheter being held in the other. The hand holding the protective tip guides it into the urethra, and then the other hand may be used to move the funnel proximally with respect to the protective tip, thereby moving the proximal end of the catheter out of the protective tip and into the urethra. If practicing such a method of usage, it may be preferred to employ a urinary catheter assembly having a relatively rigid catheter, as described above, so that the catheter has sufficiently column strength to disengage from or overcome the frictional forces applied by the protective tip and move through the urethra without collapsing or buckling before the proximal end of the catheter reaches the bladder. It may also be advantageous for the catheter to have sufficient torsional strength to transmit a rotational force applied at the distal end to the proximal end, if the protective tip is configured to be disassociated from the catheter upon rotational movement of the catheter, as described above.

Additional Aspects and Implementations

Aspects of the present subject matter described above may be beneficial alone or in combination with one or more other aspects. Without limiting the foregoing description, in accordance with one aspect of the subject matter herein, there is provided a protective tip for use in combination with a urinary catheter of the type having at least one eye. The protective tip includes a generally tubular body portion defining an interior cavity and at least one projection extending into the interior cavity of the body portion. The projection is configured to be at least partially received by an eye of a urinary catheter at least partially positioned within the body portion.

In accordance with another aspect which may be used or combined with the preceding aspect, the projection includes an inclined surface configured to be at least partially received by an eye of a urinary catheter at least partially positioned within the body portion.

In accordance with another aspect which may be used or combined with the preceding aspect, the body portion extends between a distal end and a proximal end and the inclined surface of the projection faces the proximal end.

In accordance with another aspect which may be used or combined with any of the preceding aspects, the projection includes a radial surface facing the proximal end and configured to be at least partially received by an eye of a urinary catheter at least partially positioned within the body portion.

In accordance with another aspect which may be used or combined with any of the preceding aspects, the projection extends generally radially inwardly from the body portion.

In accordance with another aspect which may be used or combined with any of the preceding aspects, the projection is integrally formed with the body portion.

In accordance with another aspect which may be used or combined with any of the preceding aspects, an insert is associated with the body portion, with the projection extending from the insert.

In accordance with another aspect which may be used or combined with the preceding aspect, the insert is fully received within the interior cavity of the body portion.

In accordance with another aspect which may be used or combined with any of the preceding two aspects, the insert further includes a guide configured to orient the projection with respect to an eye of a urinary catheter at least partially positioned within the body portion.

In accordance with another aspect which may be used or combined with any of the preceding aspects, a second projection extending into the interior cavity of the body portion and configured to be at least partially received by a second eye of a urinary catheter at least partially positioned within the body portion.

In accordance with another aspect which may be used or combined with any of the first six aspects, the protective tip is comprised of a proximal piece and a distal piece.

In accordance with another aspect which may be used or combined with the preceding aspect, the distal piece includes a fixed portion secured to the proximal piece, a free portion positioned distally of the fixed portion, and a frangible portion positioned between the fixed and free portions and configured to be broken to separate the fixed and free portions.

In accordance with another aspect which may be used or combined with the eleventh aspect, the protective tip is comprised of a proximal piece and a separate distal piece.

In accordance with another aspect, there is provided a protective tip for use in combination with a urinary catheter. The protective tip includes a generally tubular body portion defining an interior cavity and at least one projection extending into the interior cavity of the body portion. The projection is configured to apply a generally uniform frictional force to an outer surface of a urinary catheter at least partially positioned within the body portion during use of the protective tip and the urinary catheter.

In accordance with another aspect which may be used or combined with the preceding aspect, a plurality of projections extend into the interior cavity of the body portion and are configured to apply a generally uniform frictional force to an outer surface of a urinary catheter at least partially positioned within the body portion during use of the protective tip and the urinary catheter.

In accordance with another aspect which may be used or combined with the preceding aspect, the plurality of projections are substantially identical.

In accordance with another aspect which may be used or combined with any of the preceding three aspects, the projection is configured to be substantially stationary during use of the protective tip and urinary catheter.

In accordance with another aspect which may be used or combined with any of the preceding four aspects, an insert associated with the body portion, wherein the at least one projection extends from the insert.

In accordance with another aspect which may be used or combined with the preceding aspect, the insert is fully received within the interior cavity of the body portion.

In accordance with another aspect which may be used or combined with any of the fourteenth through seventeenth aspects, the protective tip is comprised of a proximal piece and a distal piece.

In accordance with another aspect, there is provided a urinary catheter assembly including a protective tip, a urinary catheter, and a tether. The urinary catheter extends between proximal and distal ends, with its proximal end being at least partially receivable within the protective tip. The tether extends between the protective tip and the distal end of the urinary catheter.

In accordance with another aspect which may be used or combined with the preceding aspect, a funnel is associated with the distal end of the urinary catheter, with the tether extending between the protective tip and the funnel.

In accordance with another aspect which may be used or combined with any of the preceding two aspects, the protective tip includes an open distal end, with the tether being configured to prevent removal of the proximal end of the urinary catheter from the open distal end of the protective tip without bending the urinary catheter.

In accordance with another aspect which may be used or combined with any of the preceding three aspects, a plurality of tethers extend between the protective tip and the distal end of the urinary catheter.

In accordance with another aspect, there is provided a urinary catheter assembly, which includes a urinary catheter and a protective tip received on the urinary catheter. The protective tip includes a proximal piece and a distal piece, with the distal piece being separate from or detachably connected to the proximal piece.

In accordance with another aspect which may be used or combined with the preceding aspect, the distal piece of the protective tip is associated with a distal end of the urinary catheter prior to use.

In accordance with another aspect which may be used or combined with the preceding aspect, the distal end of the urinary catheter includes a funnel, with the distal piece of the protective tip being detachably connected to the funnel prior to use.

In accordance with another aspect which may be used or combined with the preceding aspect, the proximal piece of the protective tip is detachably connected to the distal piece prior to use, the proximal and distal pieces of the protective tip are movable along the urinary catheter from the distal end of the urinary catheter to a proximal end of the urinary catheter, and the distal piece is configured to be detached from the proximal piece when the proximal piece has been moved to the proximal end of the urinary catheter.

In accordance with another aspect which may be used or combined with the twenty-seventh aspect, the proximal piece of the protective tip is separate from the distal piece and associated with a proximal end of the urinary catheter prior to use.

In accordance with another aspect which may be used or combined with the twenty-fifth aspect, the urinary catheter extends between proximal and distal ends, the proximal piece of the protective tip is associated with the proximal end of the urinary catheter prior to use, and the distal piece of the protective tip is separate from the proximal piece and positioned between the proximal and distal ends of the urinary catheter prior to use.

In accordance with another aspect, there is provided a protective tip for use in combination with a urinary catheter having a proximal extension with an enlarged end and a necked-down section positioned adjacent to and distally of the enlarged end. The protective tip includes an outer member and an insert at least partially received within the outer member. The insert includes a generally radially inwardly extending projection configured to be positioned distally of the enlarged end of the urinary catheter and to contact the enlarged end of the urinary catheter to resist distal movement of the urinary catheter with respect to the protective tip.

In accordance with another aspect which may be used or combined with the preceding aspect, the projection is generally annular.

In accordance with another aspect which may be used or combined with any of the preceding two aspects, the projection is hingedly associated with the remainder of the insert.

In accordance with another aspect, there is provided a urinary catheter assembly, which includes a urinary catheter and a protective sleeve tip. The urinary catheter includes a proximal end portion defining at least one eye. The protective sleeve tip is formed of a thin film material and defines an interior cavity receiving the proximal end portion of the urinary catheter. The protective sleeve tip includes at least one projection extending into the interior cavity and at least partially received by the eye of the urinary catheter.

In accordance with another aspect which may be used or combined with the preceding aspect, the urinary catheter assembly includes a distal piece associated with the protective sleeve tip, with the distal piece being comprised of a molded material.

In accordance with another aspect which may be used or combined with the preceding aspect, the protective sleeve tip is comprised of a polyurethane material and the distal piece is comprised of a polyvinyl chloride material.

In accordance with another aspect which may be used or combined with the thirty-fourth aspect, the urinary catheter is fully received within the protective sleeve tip.

In accordance with another aspect which may be used or combined with any of the preceding four aspects, the projection comprises a portion of the thin film material detachably connected to the urinary catheter.

In accordance with another aspect which may be used or combined with any of the preceding five aspects, the eye is defined in a lateral wall of the proximal end portion of the urinary catheter.

In accordance with another aspect which may be used or combined with any of the thirty-fourth through thirty-eighth aspects, the eye is defined in a proximal end of the proximal end portion of the urinary catheter.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A urinary catheter assembly, comprising:
a urinary catheter including a lateral wall with an inner surface defining a lumen, and a proximal end portion defining at least one eye in the lateral wall; and
a protective sleeve tip defining an interior cavity receiving the proximal end portion of the urinary catheter, wherein the protective sleeve tip is formed of a thin film material and includes at least one projection
extending into the interior cavity,
at least partially received by the at least one eye of the urinary catheter, and
detachably secured to the inner surface of the urinary catheter at a location opposite the at least one eye.

2. The urinary catheter assembly of claim 1, further comprising a distal piece associated with the protective sleeve tip, wherein the distal piece is comprised of a molded material.

3. The urinary catheter assembly of claim 2, wherein the protective sleeve tip is comprised of a polyurethane material and the distal piece is comprised of a polyvinyl chloride material.

4. The urinary catheter assembly of claim 1, wherein the urinary catheter is fully received within the protective sleeve tip.

5. A urinary catheter assembly, comprising
a urinary catheter including a proximal end portion defining first and second eyes;
a protective sleeve tip defining an interior cavity receiving the proximal end portion of the urinary catheter; and
a distal piece associated with the protective sleeve tip, wherein
the protective sleeve tip is formed of a thin film material and includes a first projection comprising a portion of the protective sleeve tip and at least partially received by the first eye,
the distal piece includes a second projection extending from the distal piece and at least partially received by the second eye, and
the protective sleeve tip and the distal piece are formed of different materials.

6. The urinary catheter assembly of claim 5, wherein first projection is detachably connected to the urinary catheter.

7. The urinary catheter assembly of claim 5, wherein the first and second eyes are defined in a lateral wall of the proximal end portion of the urinary catheter.

8. A method of manufacturing a urinary catheter assembly, comprising:
providing a urinary catheter including a lateral wall with an inner surface defining a lumen, and a proximal end portion defining at least one eye in the lateral wall;
positioning the proximal end portion of the urinary catheter within a protective sleeve tip at least partially formed of a thin film material;
advancing a portion of the thin film material into the at least one eye of the urinary catheter; and
detachably securing said portion of the thin film material to the inner surface of the urinary catheter at a location opposite the at least one eye.

9. The method of claim 8, further comprising providing the protective sleeve tip with an associated distal piece formed of a different material than the protective sleeve tip.

10. The method of claim 9, wherein
said providing a urinary catheter includes providing a urinary catheter including a proximal end portion defining a first eye and a second eye,
said providing a protective sleeve tip includes providing a distal piece comprising a projection,
said advancing a portion of the thin film material into the eye of the at least one eye of the urinary catheter includes advancing said portion of the thin film material into the first eye, and further comprising
advancing a portion of the projection of the distal piece into the second eye.

11. The method of claim 9, wherein the thin film material is comprised of a polyurethane material and the distal piece is comprised of a polyvinyl chloride material.

12. The method of claim 8, wherein
said providing a urinary catheter includes providing a urinary catheter comprising a shaft extending between said proximal end portion and a distal end portion, with a funnel associated with said distal end portion, and
said positioning the proximal end portion of the urinary catheter within a protective sleeve tip includes positioning the entire catheter shaft within the protective sleeve tip.

13. The method of claim 12, further comprising sealing the protective sleeve tip to the funnel of the urinary catheter.

* * * * *